US008222029B2

(12) United States Patent
Charneau et al.

(10) Patent No.: US 8,222,029 B2
(45) Date of Patent: *Jul. 17, 2012

(54) LENTIVIRAL VECTOR-BASED VACCINE

(75) Inventors: Pierre Charneau, Paris (FR); Philippe Despres, La Garenne Colombes (FR)

(73) Assignee: Institut Pasteur, Paris (FR)

( * ) Notice: Subject to any disclaimer, the term of this patent is extended or adjusted under 35 U.S.C. 154(b) by 614 days.

This patent is subject to a terminal disclaimer.

(21) Appl. No.: 12/083,532

(22) PCT Filed: Oct. 17, 2006

(86) PCT No.: PCT/IB2006/003931
§ 371 (c)(1),
(2), (4) Date: Apr. 6, 2009

(87) PCT Pub. No.: WO2007/052165
PCT Pub. Date: May 10, 2007

(65) Prior Publication Data
US 2011/0086065 A9    Apr. 14, 2011

Related U.S. Application Data

(63) Continuation-in-part of application No. 11/250,616, filed on Oct. 17, 2005, and a continuation-in-part of application No. 11/596,675, filed as application No. PCT/IB2005/001753 on May 16, 2005, now abandoned.

(51) Int. Cl.
*C12N 15/00* (2006.01)
*A61K 48/00* (2006.01)
(52) U.S. Cl. ............. 435/320.1; 435/325; 435/440; 435/455; 424/93.2
(58) Field of Classification Search .............. None
See application file for complete search history.

(56) References Cited

U.S. PATENT DOCUMENTS

| 5,883,081 | A | 3/1999 | Kraus et al. |
| 6,498,033 | B1 | 12/2002 | Dropulic et al. |
| 6,682,907 | B1 * | 1/2004 | Charneau et al. ............ 435/69.1 |
| 6,870,032 | B1 | 3/2005 | Flamand et al. |
| 7,052,830 | B1 | 5/2006 | Branch et al. |
| 7,968,332 | B2 | 6/2011 | Charneau et al. |
| 7,981,671 | B2 | 7/2011 | Charneau et al. |
| 2003/0104611 | A1 | 6/2003 | Johnston et al. |
| 2003/0194392 | A1 | 10/2003 | Charneau et al. |
| 2004/0009469 | A1 | 1/2004 | Apt et al. |
| 2004/0037848 | A1 | 2/2004 | Audonnet et al. |
| 2004/0081636 | A1 | 4/2004 | Charneau et al. |
| 2006/0040347 | A1 | 2/2006 | Charneau et al. |
| 2006/0073164 | A1 | 4/2006 | Tangy et al. |
| 2007/0087354 | A1 | 4/2007 | Charneau et al. |
| 2007/0224679 | A1 | 9/2007 | Charneau et al. |
| 2009/0214589 | A1 | 8/2009 | Despres et al. |
| 2010/0028382 | A1 | 2/2010 | Charneau et al. |
| 2010/0221820 | A1 | 9/2010 | Charneau et al. |
| 2011/0206710 | A1 | 8/2011 | Despres et al. |

FOREIGN PATENT DOCUMENTS

| CA | 2456873 A1 | 8/2004 |
| EP | 1092779 A1 | 4/2001 |
| FR | 2777909 A1 | 10/1999 |
| WO | WO 99/55892 A1 | 11/1999 |
| WO | WO 00/75665 A1 | 12/2000 |
| WO | WO 01/27300 A1 | 4/2001 |
| WO | WO-2004/076619 A2 | 9/2004 |

OTHER PUBLICATIONS

Despres et al. (Journal of Infectious Diseases, Jan. 2005, vol. 191, p. 207-214) in parent 11/250,616.*
Sirven et al. (Molecular Therapy, Apr. 2001, vol. 3, p. 438-448) in parent 11/250,616.*
Rohrlich et al. (Human Immunology, May 2004, vol. 54, p. 514-522) in parent 11/250,616.*
Despres et al. (Journal of Infectious Diseases, Jan. 2005, vol. 191, p. 207-214).*
Pletnev et al., "Molecularly engineered live-attenuated chimeric West Nile/dengue virus vaccines protect rhesus monkeys from West Nile virus", Virology, vol. 314, pp. 190-195 (2003).
Pletnev et al., West Nile virus/dengue type 4 virus chimeras that are reduced in neurovirulence and peripheral virulence without loss of immunogenicity or protective efficacy, PNAS, vol. 99, No. 5, pp. 3036-3041 (2002).
Puthenveetil et al., "Successful correction of the human p-thalassemia major phenotype using a lentiviral vector", Blood, vol. 104, No. 12, pp. 3445-3453 (2004).
Ralph et al., "Silencing mutant SOD1 using RNAi protects against neurodegeneration and extends survival in an ALS model", Nature Medicine, vol. 11, No. 4, pp. 429-433 (2005).
Seligman et al., "Live flavivirus vaccines: reasons for caution", The Lancet, vol. 363, pp. 2073-2075 (2004).
Shrestha et al., "Role of CD8*T Cells in Control of West Nile Virus Infection", Journal of Virology, vol. 78, No. 15, pp. 8312-8321 (2004).
Sirven et al., "The human immunodeficiency virus type-1 central DNA flap is a crucial determinant for lentiviral vector nuclear import and gene transduction of human hematopoietic stem cells", Blood, vol. 96, No. 13, pp. 4103-4110 (2000).
Iglesias et al.; "A Single Immunization With a Minute Dose of a Lentiviral Vector-Based Vaccine is Highly Effective at Eliciting Protective Humoral Immunity Against West Nile Virus"; The Journal of Gene Medicine, vol. 8, No. 3, pp. 265-274, (2003).
Després et al.; "Live Measles Vaccine Expressing the Secreted Form of the West Nile Virus Envelope Glycoprotein Protects Against West Nile Virus Encephalitis"; Journal of Infectious Diseases, vol. 191, No. 2, pp. 207-214, (2005).

(Continued)

*Primary Examiner* — Agnieszka Boesen
(74) *Attorney, Agent, or Firm* — Law Office of Salvatore Arrigo and Scott Lee, LLP

(57) ABSTRACT

Methods of eliciting humoral responses, methods of immunization, and methods of vaccination using lentiviral vector are disclosed. Additionally, immunogenic compositions and vaccines for West Nile Virus are disclosed.

22 Claims, 7 Drawing Sheets

OTHER PUBLICATIONS

Zarei et al.; "Lentiviral Transduction of Dendritic Cells Confers Protective Antiviral Immunity In Vivo"; Journal of Virology, vol. 78, No. 14, pp. 7843-7845, (2004).
He et al.; "Immunization With Lentiviral Vector-Transduced Dendritic Cells Induces Strong and Long-Lasting T Cell Responses and Therapeutic Immunity"; Journal of Immunology, vol. 174, No. 6, pp. 3808-3817, (205).
Wang et al.; "Immunization of Mice Against West Nile Virus With Recombinant Envelope Protein"; Journal of Immunoloy, vol. 167, pp. 5273-5277, (2001).
Wiznerowicz et al.; "Harnessing HIV for Therapy, Basic Research and Biotechnology"; Trends in Biotechnology, vol. 23, No. 1, pp. 42-47, (2005).
Bartosch et al.; "Infectious Hepatitis C Virus Pseudo-Particles Containing Functional EI-E2 Envelope Proteins Complexes"; J.Exp. Med, vol. 197, No. 5, pp. 6333-642, (2003).
Colombage et al.; "DNA-Based and Aplha Virus-Vectored Immunisation With PrM and E Protein Elicits Long-Lived and Protective Immunity Against the Flavivirus, Murray Valley Encephalitis Virus"; Virology, vol. 250, pp. 151-163, (1998).
Malkinson et al., Emerging Infectious Diseases, 2002, 8(4):392-397.
Takahashi et al., "Rescue from Photoreceptor Degeneration in the rd Mouse by Human Immunodeficiency Virus Vector-Mediated Gene Transfer", Journal of Virology, vol. 73, No. 9, pp. 7812-7816 (1999).
Tonry et al., "Persistent Shedding of West Nile Virus in Urine of Experimentally Infected Hamsters", Am. J. Trop. Med. Hyg., vol. 72, No. 3, pp. 320-324 (2005).
Vandendriessche et al., Lentiviral vectors containing the human immunodificency virus type-1 central polypurine tract can efficiently transduce nondividing hepatocytes and antigen-presenting cells in vivo, Blood, vol. 100, No. 3, pp. 813-822 (2002).
Wang et al., "Immunization of Mice Against West Nile Virus with Recombinant Envelope Protein", The Journal of Immunology, vol. 167, pp. 5273-5277 (2001).
Yee et al., "A general method for the generation of high-titer, pantropic retroviral vectors: Highly efficient infection of primary hepatocytes", P.N.A.S., USA, vol. 91, pp. 9564-9568 (1994).
Zarei, et al., "Lentiviral Transduction of Dendritic Cells Confers Protective Antiviral Immunity In Vivo", Journal of Virology, vol. 78, No. 14, pp. 7843-7845 (2004).
Zennou et al., "HIV-1 Genome Nuclear Import Is Mediated by a Central DNA Flap", Cell, vol. 101, pp. 173-185 (2000).
Zennou et al., "The HIV-1 DNA flap stimulates HIV vector-mediated cell transduction in the brain", Nature Biotechnology, vol. 19, pp. 446-450 (2001).
Zufferey et al., "Multiply attenuated lentiviral vector achieves efficient gene delivery in vivo", Nature Biotechnology, vol. 15, pp. 871-875 (1997).
Daupin et al. Vaccine, 2007, vol. 25, p. 5563-5576.
Berthet et al. Journal of General Virology, 1997, vol. 78, p. 2293-2297.
Arroyo et al., "ChimeriVax-West Nile Virus Live-Attenuated Vaccine: Preclinical Evaluation of Safety, Immunogenicity, and Efficacy", Journal of Virology, vol. 78, No. 22, pp. 12497-12507 (2004).
Beasley et al., "Identification of Neutralizing Epitopes within Structural Domain III of the West Nile Virus Envelope Protein", Journal of Virology, vol. 76, No. 24, pp. 13097-13100 (2002).
Benhamida, et al., "Transduced CD34" Cells from Adrenoleukodystrophy Patients with HIV-Derived Vector Mediate Long-Term Engraftment of NOD/SCID Mice, Molecular Therapy, vol. 7, No. 3, pp. 317-324 (2003).
Ben-Nathan et al., "Prophylactic and Therapeutic Efficacy of Human Intravenous Immunoglobulin in Treating West Nile Virus Infection in Mice", The Journal of Infectious Disease, vol. 188, pp. 5-12 (2003).
Biffi et al., "Correction of metachromatic leukodystrophy in the mouse model by transplantation of genetically modified hematopoietic stem cells", The Journal of Clinical Investigation, vol. 113, No. 8, pp. 1118-1129 (2004).
Breckpot et al., "Lentivirally transduced dendritic cells as a tool for cancer immunotherapy", The Journal of Gene Medicine, vol. 5, pp. 654-667 (2003).
Brussel et al., "Analysis of Early Human Immunodeficiency Virus Type 1 DNA Synthesis by Use of a New Sensitive Assay for Quantifying Integrated Provirus", Journal of Virology, vol. 77, No. 18, pp. 10119-10124 (2003).
Ceccaldi et al., "New insights on the neuropathogenicity of West Nile virus", FEMS Microbiology Letters, vol. 233, pp. 1-6 (2004).
Charrel et al., "Evolutionary relationship between Old World West Nile virus strains Evidence for viral gene flow between Africa, the Middle East, and Europe", Virology, vol. 315, pp. 381-388 (2003).
Dauphin et al., "West Nile: worldwide current situation in animals and humans", Comp. Immun. Microbiol. Infect. Dis., vol. 27, pp. 343-355 (2004).
Davis et al., "West Nile Virus Recombinant DNA Vaccine Protects Mouse and Horse from Virus Challenge and Expresses in Vitro a Noninfectious Recombinant Antigen That Can Be Used in Enzyme-Linked Immunosorbent Assays", Journal of Virology, vol. 75, No. 9, pp. 4040-4047 (2001).
Despres et al., "Differences between Cell Membrane Fusion Activities of Two Dengue Type-1 Isolates Reflect Modifications of Viral Structure", Virology, vol. 196, pp. 209-219 (1993).
Despres et al., "Effects of Anti-E2 Monoclonal Antibody on Sindbis Virus Replication in AT3 Cells Expressing bcl-2", Journal of Virology, vol. 69, No. 11, pp. 7006-7014 (1995).
Deubel, et al., "Variations in Biological Features of West Nile Viruses", Annals New York Academy of Sciences, vol. 951, pp. 195-206 (2001).
Diamond et al., "A Critical Role for Induced IgM in the Protection against West Nile Virus Infection", J. Exp. Med., vol. 198, No. 12, pp. 1853-1862 (2003).
Diamond et al., "B Cells and Antibody Play Critical Roles in the Immediate Defense of Disseminated Infection by West Nile Encephalitis Virus", Journal of Virology, vol. 77, No. 4, pp. 2578-2586 (2003).
Dyall et al., "Lentivirus-transduced human monocyte-derived dendritic cells efficiently stimulate antigen-specific cytotoxic T lymphocytes", Gene Therapy, vol. 97, No. 1, pp. 114-121 (2001).
Engle et al., "Antibody Prophylaxis and Therapy against West Nile Virus Infection in Wild-Type and Immunodeficient Mice", Journal of Virology, vol. 77, No. 24, pp. 12941-12949 (2003).
Esslinger et al., "Efficient Transduction of Dendritic Cells and Induction of a T-Cell Response by Third-Generation Lentivectors", Human Gene Therapy, vol. 13, pp. 1091-1100 (2002).
Esslinger et al., "In vivo administration of a lentiviral vaccine targets DCs and induces efficient CD8+ T cell responses", The Journal of Clinical Investigation, vol. 111, No. 11, pp. 1673-1681 (2003).
Firat et al., "Use of lentiviral flap vector for induction of CTL immunity against melanoma. Perspectives for immunotherapy", The Journal of Gene Medicine, vol. 4, pp. 38-45 (2002).
Giannini et al., "A Highly Efficient, Stable, and Rapid Approach for Ex Vivo Human Liver Gene Therapy Via a FLAP Lentiviral Vector", Hepatology, vol. 38, No. 1, pp. 114-122 (2003).
Gould et al., "Evolution and dispersal of encephalitic flaviviruses", Archives of Virology Suppl, vol. 18, pp. 65-84 (2004).
Hacein-Bey-Abina et al., "LMO2-Associated Clonal T Cell Proliferation in Two Patients after Gene Therapy for SCID-X1", Science, vol. 302, pp. 415-419 (2003).
He et al., "Immunization with Lentiviral Vector-Transduced Dendritic Cells Induces Strong and Long-Lasting T Cell Responses and Therapeutic Immunity", The Journal of Immunology, vol. 174, pp. 3808-3817 (2005).
Kootstra et al., "Efficient Production of Human FVIII in Hemophilic Mice Using Lentiviral Vectors", Molecular Therapy, vol. 7, No. 5, pp. 623-631 (2003).
Kordower et al., "Neurodegeneration Prevented by Lentiviral Vector Delivery of GDNF in Primate Models of Parkinson's Disease", Science, vol. 290, pp. 767-773 (2000).
Lanciotti et al., "Complete Genome Sequences and Phylogenetic Analysis of West Nile Virus Strains Isolated from the United States, Europe, and the Middle East", Virology, vol. 298, pp. 96-105 (2002).
Lucas et al., "The Israeli strain IS-98-STI of West Nile virus as viral model for West Nile encephalitis in the Old World", Virology Journal, vol. 1, No. 9 (2004).

Mashimo et al., "A nonsense mutation in the gene encoding 2'-5'-oligoadenylate synthetase/L1 isoform is associated with West Nile virus susceptibility in laboratory mice", P.N.A.S., vol. 99, No. 17, pp. 11311-11316 (2002).

Metharom et al., "Lentiviral Vector-Mediated Tyrosinase-Related Protein 2 Gene Transfer to Dendritic Cells for the Therapy of Melanoma", Human Gene Therapy, vol. 12, pp. 2203-2213 (2001).

Minke et al., "Recombinant canarypoxvirus vaccine carrying the prM/E genes of West Nile virus protects horses against a West Nile virus-mosquito challenge", Archives of Virology Suppl, vol. 18, pp. 221-230 (2004).

Nguyen et al., "Highly Efficient Lentiviral Vector-Mediated Transduction of Nondividing, Fully Reimplantable Primary Hepatocytes", Molecular Therapy, vol. 6, No. 2, pp. 199-209 (2002).

Nusbaum et al., "Absence of Humoral Response in Flamingos and Red-Tailed Hawks to Experimental Vaccination with a Killed West Nile Virus Vaccine", Avian Diseases, vol. 47, pp. 750-752 (2003).

Palmowski et al., Intravenous Injection of a Lentiviral Vector Encoding NY-ESO-1 Induces an Effective CTL Response, The Journal of Immunology, vol. 172, pp. 1582-1587 (2004).

Pawliuk et al., "Correction of Sickle Cell Disease in Transgenic Mouse Models by Gene Therapy", Science, vol. 294, pp. 2368-2371 (2001).

Park et al, Therapeutic levels of human factor VIII and IX using HIV-1—based lentiviral vectors in mouse liver, Blood. 2000;96:1173-1176.

Follenzi et al, Targeting lentiviral vector expression to hepatocytes limits transgene-specific immune response and establishes long-term expression of human antihemophilic factor IX in mice, Blood. 2004;103:3700-3709.

* cited by examiner

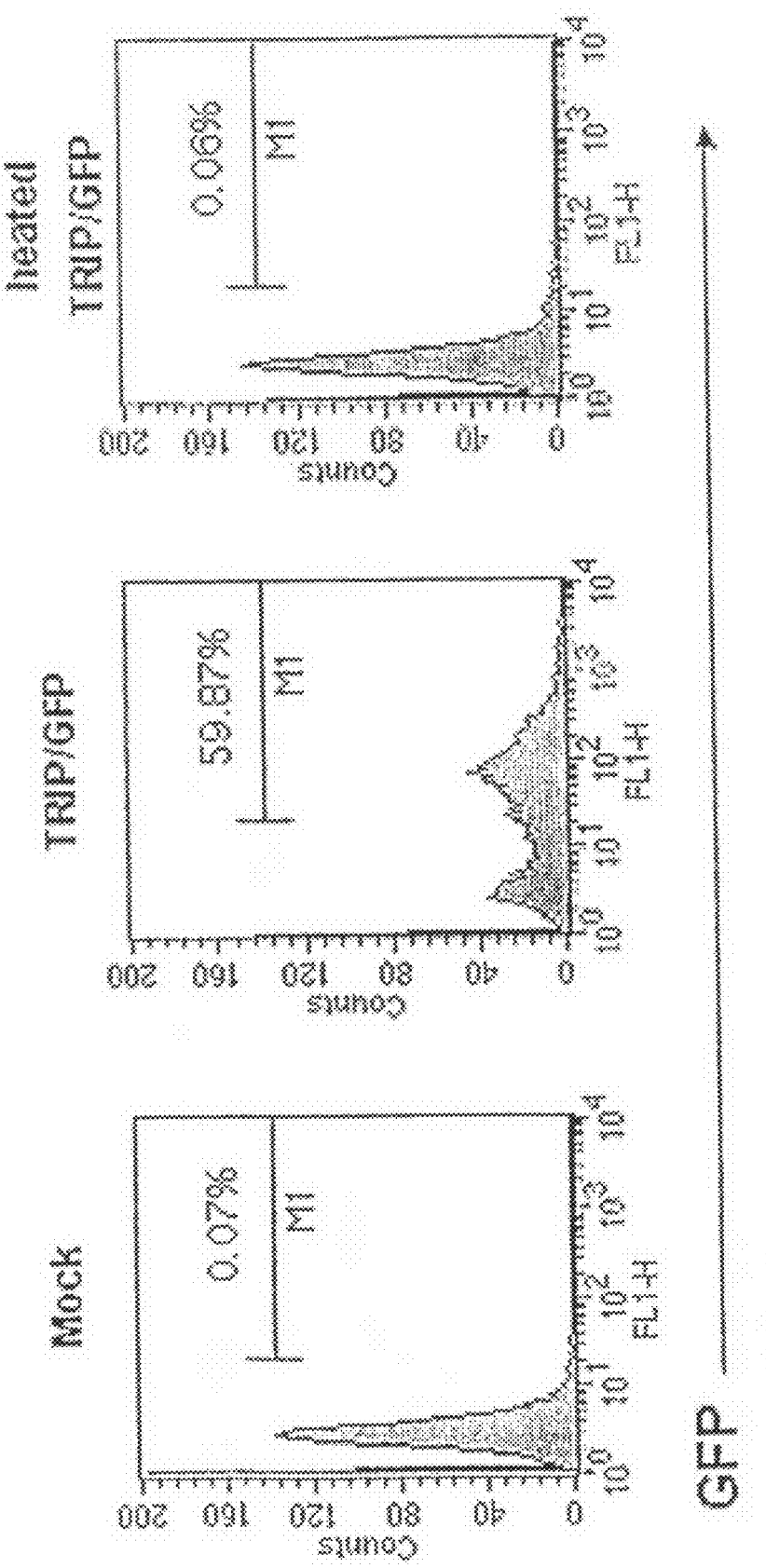

```
atgagagttgtgtttgtcgtgctattgcttttggtggccccagcttacagcttc
aactgccttggaatgagcaacagagacttcttggaaggagtgtctggagcaaca
tgggtggatttggttctcgaaggcgacagctgcgtgactatcatgtctaaggac
aagcctaccatcgatgtgaagatgatgaatatggaggcggtcaacctggcagag
gtccgcagttattgctatttggctaccgtcagcgatctctccaccaaagctgcg
tgcccgaccatgggagaagctcacaatgacaaacgtgctgacccagcttttgtg
tgcagacaaggagtggtggacaggggctggggcaacggctgcggattatttggc
aaaggaagcattgacacatgcgccaaatttgcctgctctaccaaggcaatagga
agaaccatcttgaaagagaatatcaagtacgaagtggccattttttgtccatgga
ccaactactgtggagtcgcacggaaactactccacacaggttggagccactcag
gcagggagattcagcatcactcctgcggcgccttcatacacactaaagcttgga
gaatatggagaggtgacagtggactgtgaaccacggtcagggattgacaccaat
gcatactacgtgatgactgttggaacaaagacgttcttggtccatcgtgagtgg
ttcatggacctcaacctcccttggagcagtgctggaagtactgtgtggaggaac
agagagacgttaatggagtttgaggaaccacacgccacgaagcagtctgtgata
gcattgggctcacaagagggagctctgcatcaagctttggctggagccattcct
gtggaattttcaagcaacactgtcaagttgacgtcgggtcatttgaagtgtaga
gtgaagatggaaaaattgcagttgagggaacaacctatggcgtctgttcaaag
gctttcaagtttcttgggactcccgcagacacaggtcacggcactgtggtgttg
gaattgcagtacactggcacggatggaccttgcaaagttcctatctcgtcagtg
gcttcattgaacgacctaacgccagtgggcagattggtcactgtcaacccttttt
gtttcagtggccacggccaacgctaaggtcctgattgaattggaaccacccttt
ggagactcatacatagtggtgggcagaggagaacaacagatcaatcaccattgg
cacaagtctggaagcagcattggcaaagcctttacaaccaccctcaaaggagcg
cagagactagccgctctaggagacacagcttgggactttggatcagttggaggg
gtgttcacctcagttgggaaggctgtctaa(SEQ ID NO: 9)
```

Figure 4

```
agagttgtgtttgtcgtgctattgcttttggtggccccagcttacagcttcaac
tgccttggaatgagcaacagagacttcttggaaggagtgtctggagcaacatgg
gtggatttggttctcgaaggcgacagctgcgtgactatcatgtctaaggacaag
cctaccatcgatgtgaagatgatgaatatggaggcggtcaacctggcagaggtc
cgcagttattgctatttggctaccgtcagcgatctctccaccaaagctgcgtgc
ccgaccatgggagaagctcacaatgacaaacgtgctgacccagcttttgtgtgc
agacaaggagtggtggacaggggctggggcaacggctgcggattatttggcaaa
ggaagcattgacacatgcgccaaatttgcctgctctaccaaggcaataggaaga
accatcttgaaagagaatatcaagtacgaagtggccattttgtccatggacca
actactgtggagtcgcacggaaactactccacacaggttggagccactcaggca
gggagattcagcatcactcctgcggcgccttcatacacactaaagcttggagaa
tatggagaggtgacagtggactgtgaaccacggtcagggattgacaccaatgca
tactacgtgatgactgttggaacaaagacgttcttggtccatcgtgagtggttc
atggacctcaacctcccttggagcagtgctggaagtactgtgtggaggaacaga
gagacgttaatggagtttgaggaaccacacgccacgaagcagtctgtgatagca
ttgggctcacaagagggagctctgcatcaagctttggctggagccattcctgtg
gaattttcaagcaacactgtcaagttgacgtcgggtcatttgaagtgtagagtg
aagatggaaaaattgcagttgagggaacaacctatggcgtctgttcaaaggct
ttcaagtttcttgggactcccgcagacacaggtcacggcactgtggtgttggaa
ttgcagtacactggcacggatggaccttgcaaagttcctatctcgtcagtggct
tcattgaacgacctaacgccagtgggcagattggtcactgtcaacccttttgtt
tcagtggccacggccaacgctaaggtcctgattgaattggaaccacccttggaa
gactcatacatagtggtgggcagaggagaacaacagatcaatcaccattggcac
aagtctggaagcagcattggcaaagcctttacaaccaccctcaaaggagcgcag
agactagccgctctaggagacacagcttgggactttggatcagttggaggggtg
ttcacctcagttgggaaggctgtc
(SEQ ID NO: 10)
```

Figure 5

RVVFVVLLLLVAPAYSFNCLGMSNRDFLEGVSGATWVDLVLEGDSCVTIMSKDK
PTIDVKMMNMEAVNLAEVRSYCYLATVSDLSTKAACPTMGEAHNDKRADPAFVC
RQGVVDRGWGNGCGLFGKGSIDTCAKFACSTKAIGRTILKENIKYEVAIFVHGP
TTVESHGNYSTQVGATQAGRFSITPAAPSYTLKLGEYGEVTVDCEPRSGIDTNA
YYVMTVGTKTFLVHREWFMDLNLPWSSAGSTVWRNRETLMEFEEPHATKQSVIA
LGSQEGALHQALAGAIPVEFSSNTVKLTSGHLKCRVKMEKLQLKGTTYGVCSKA
FKFLGTPADTGHGTVVLELQYTGTDGPCKVPISSVASLNDLTPVGRLVTVNPFV
SVATANAKVLIELEPPFGDSYIVVGRGEQQINHHWHKSGSSIGKAFTTTLKGAQ
RLAALGDTAWDFGSVGGVFTSVGKAV    (SEQ ID NO: 11)

Figure 6

TTYGVCSKAFKFLGTPADTGHGTVVLELQYTGTDGPCKVPISSVASLNDLTPVG
RLVTVNPFVSVATANAKVLIELEPPFGDSYIVVGRGEQQI    (SEQ ID NO: 12)

Figure 7

```
TGGAAGGGCTAATTCACTCCCAACGAAGACAAGATATCCTTGATCTGTGGATCTACCACACAACAAGGCTACTCCCTGATTAGCAGAACTACACCAGGGCCAGGGATCAGATATCC
ACTGACCTTTGGATGGTGCTACAAGCTAGTACCAGTTGAGCCAGAGAAGTTAGAAGAGAACAAAGCCAACAAGGAGAACACCAGCTTGTTACAACCTGTGAGCCTGCATGGGATGAC
CCGGAGAGAAGTGTTAGAGTGGAGTTTGACAGCTTCATCACGGTGGCCCGAGAGCTGCATCCGGAGTACTTCAAGAACTGCTGATATCCAGCTTGCTACAAGGA
CTTCCGCTGGGGGACTTCCAGGGAGCCTGGCTCTGGCAGCTAGGGAACCCACTGCTTAAGCCTCAATAAGCAGCTGCTTTTGCCCTGTATCTGGTCTCTCTGGTTAGA
CCAGATCTGAGCCTGGAGACCCTTTAGTCAGTGTGGAAAATCTCTAGCAGTGGCGCCCACGTTCTAAGGCGTGTGTGCCCAGGAGGGAGCTCTCGACGCAGGAGTCGGCTTGC
TAGAGATCCCGGAATTCCCGCCCACGCAAGAGGGTGAGGGCGCGGACTGTGAGTAACGGCCAAGGAGAAGCGAAAGGGAAGTAGTGTGCTTCAAGTAGTGTGTGCCCGAGGAAGCTCTGGTAAC
TGAAGGCGGGGAGAATTAGATCGCCATCGAGAACATCAGAGGCGCGATGGGAAGAAATTCGCCAAGAAATATAAAACATATAAACCATATAGTAAAGAAGAACGATTCGCAGTTAA
AGCCCTGTGTTAGAAACATCAGAGAATCTGTAGACAATACTGGACAGCAGTCCCTCAGACAGGATCAGAAGAAAAGTTAGATCATTATATACAGTAGCAACCCCTCTAT
TGTGTGCATCAAAGGATAGAGGGACAATTGGAGAAGTGAATTATATAAAATAGTAAAATTGAACCATTAGGAGTAGCACCCACCAAGCAAAGAGAAGAAGTAGCACCCCCGCTGATCTTCAGACCTGA
GGAGAGATAGGGAATAGGAGCTTTGTTCTTGGGTTCTTGGGAGCACAGGAAGCACTCTGGGCATGGGCCAGCTGCACCAGCAATTAGGAGATACCTAAAGGAT
GCAGAACAATTTGCTGAGGGTCTATTGAGCGCAACAGCATCTGTTGCAAGCACTCATTGCACCACTGCTGTGCCTTGGATAGCAAGATATTCATCAGGCCAGCAAGCATCCTGGAATGCAAGACCTGA
CAACAGCTCCTGGGATTTGGGGTTAACATTAACAAGTTATTGTGTATAAAACCACTGTGTATATAAATTATTCATAGATGAATCGAATCGAATCAAATGAATCATTAGCAAGCATTGCGATCTGAATAGA
TTTGTGGAATTGTTTAACATACAAGCTTATAATACACTCCTTAATTGAAGAATCGCAAAAACCAGGTCTGGTAGTTCATAATGATATAGGAGGCTTGGTAGTTTAAGAGGCTTGGTACTTTCTATAGTGAATAGA
GTTAGGCAGGGATATCGCAGGATCCGAATTCACACTGTCGAATTTCATCCACAAATTTaaagaaaaggggggATTGGGGGTACAGTGGGGCGATAAGCTTGGGAGTTCCG
GATTAGTGAACGACATCAAAACTAAAGAATTACAAAACAAATTACaaaattttcGGGGGTTATTACAGGGGATTAAAGAAGGTGAGAGAGAAGAATAGAGAGATAGACATA
ATAGCAACAGACATATCAACTTACGGTATTATGGGACTTTCCACCGATTAAGACAGACAGCTCGTTAGTGAACCGTCAGAGCTCTACAGCTTCAACTGCCTTGAATGAGCAACAGAGACTTCTTGAAGGGGGGCTCTGCAGACATGGGTGG
CGTTACATAACTACGGTATTTTATGGGACTTTATCGGTAAACTGCCCACTTGGCAGTACATCAAGTGTATCATCACGTATCATCGCTATTAGTGACATGCAACAACTCGCTTAACTGTGATAGTGATAGT
CAATGGTGGAGTATTTCCAAGTCTCCACCCATTGACGTCAATGGGAGTCCTCCATTGATGGCTATTAGTGAGACTATAGCTACCATTGACGTCAATGGGCGTGGATAGCGGTTTGACTC
ACGGGGATTTCCAAGTCTCCACCCCATTGACGTCAATGGGAGTTTGTTTTGGCACCAAAATCAACGGGACTTTCCAAAATGTCGTAACAAGCAACCGCCTGACGCACCGCACCGACTCTAGAgaCGT
AGGCCGTGTACGGTGGGAGGTCTATATAAGCAGACGCTGTTAGTGAACCGTCAGCTCAGCTTGACTTCAGAGCTTCAACTGCCTTGGGCCCAGCTTACAGCTTCAACTGCCCCAGCTTGGGCCAGCTTGGGCCCAGCTTACAGCTTCAACTGCCCCAGCTTGGGCCCAGCTTGGGCCAGCTTGGGCCAGCTTACACGT
ACGATGAGAGTTGTTGTTCGTGATTGCTTATTGCTGCTGACTATCATGTCCGTGACTATCATGTCGCGTGACCATCAAGCTGCACCATCATGACACACGGGTCCCCGCAAAGCCATGAATGATGATCAAACGTGCTGACCCAGCTTTGTCCAGCGTGTCCGTGCAGGTGCAGAGGTCCGCAGTTATTGCTA
ATTTGGTTCACCGTGCAAGCCGACGATCCTGCCGATTATTTGCCAACAACGAAGAAGCATCGCAACGCTGCCCACCAAAGCTGCCCAAAGCTGCCCCAAGCAATCTGAAGCAATCTGCAAGCTGAAGCAATCTGAAGACACTACACACTAAA
TGGGGCCAACGCGTGCGGATGGACCAACTACTGTGGACCAACTACTGTGGAGACGTGAGAACAGAATCGTTCGCACGTTCCTTGGTGTCACATCGACGTCATCCTGCCGGGGAACAAGCCCTCCAAGAACGCGCCCGCTCTTGGCACTGCATGGCCACACTAA
CCATTTTGTCGAGAATATGGAGGTGACAGTGACTGTGACAGTGACTGGGTGACAGTGGCAAGGAACTGGCAGACGCCAACATGCGCAAGACACGGCTGGACCATCTCCAACGCGCCCACGGCCACTCCTGCACGTCTCACTACACGTCTTGGTCCACATCGTGAGATGGCTCAC
AAGAAGAGGGAGCTGGTCATCAAGGTCTGTGAGCCATTGGGGACCTCAACCCCAGGGGGAACTTTGGGACTTTCTGAAGTTCACAGGCTTGGGCAGGTCGGAGTCAGAATCTGTGGTTAACAAGAATTGCAGTT
GAAGGGAACAACCTATGGCGTCGTCTTCAGTGGCTTCAATTGAACCGACCTAAGCCAGTGGGCAGTCCCAGATCAATCACGATTGGCACAAGTCTGGAAGCAGGGTCGAGAATTTGCAACACTGTGGGTGTTGAAGGCCCACGCGATGGACCTTGC
AACCACCCTTTGGAGATCTTGGAGACTCCGCTCAGGACTTGGGGACTTTGGACTTTGGGCAGGAGGAGAACAACAGATCAATCACCATTGGCACAAGTCTGGCCAAGCCTTTAAGACCACCCTTAAGACCACCCTTAAGACCACCCTCAAAGGAGC
AGGGCAGCTGAGATCTTTAGCGCGCCGTCTAGGAGACTCAGGATCCTGGACATTGTGGGGACATTGGGACTTTGGGACTTTGGGACTTGGGACTTGGATGTCCAGTTGGGACTACCTGGGCCTACCTTTAAGACCAATGACTTACA
TGTACTGGGTCTCTCTGGTTAGACCAGATCTGAGCCTGGAGCTCTCTGGCTAACTAGGGAACCCACTGCTTAAGCCTCAATAAAGCTTGCCTTGAGTGCTTCAAGTAGTGTGTGCCC
GTCTGTGTTGTGACTCTGGTAACTAGAGATCCCTCAGACCCTTTAGTCAGTGTGGAAAATCTCTAGCAGT (SEQ ID NO: 13)
```

Figure 8

LENTIVIRAL VECTOR-BASED VACCINE

This application is the National Stage of International Application PCT/IB2006/003931, filed Oct. 17, 2006, which is a continuation-in-part of U.S. application Ser. No. 11/250,616, filed on Oct. 17, 2005. This application is also a continuation-in-part of U.S. application Ser. No. 11/596,675, filed on Aug. 4, 2008 (now abandoned), which was the National Stage of International Application PCT/IB2005/001753, filed May 16, 2005, which claims the benefit of Appln. FR 0405366, filed on May 17, 2004, in France.

FIELD OF THE INVENTION

The invention is directed to lentiviral vector, methods of gene transfer, immunization, and vaccination using lentiviral vector, processes for the production of recombinant polypeptides, antibodies generated against these polypeptides, and the use of such molecules in diagnostic methods, kits, immunogenic compositions, vaccines, and antiviral therapy.

BACKGROUND OF THE INVENTION

In the past few years, lentiviral gene transfer vectors have gained a considerable interest among the gene therapy community. This unmatched reputation is due to their ability to efficiently and stably transfer therapeutic or reporter genes to a large variety of cells and tissues of key importance for therapeutic intervention, such as hematopoietic stem cells, brain, liver and retina (see [1-4], among others). Lentiviral vectors achieve high transduction efficiency irrespective of the proliferative status of the target cells, thus circumventing one of the main limitations of oncovirus-derived retroviral vectors in which transduction is restricted to dividing cells.

This advantage is reflected in a number of successful preclinical tests in various animal models of human diseases (see [5-11], among others), and will undoubtedly translate into their exploitation in a growing number of clinical trials.

More recently, lentiviral vectors have also been proven as promising vaccination vectors. Most studies to date have focused on the induction of cellular immune responses in the field of anti-tumoral immunotherapy [12-18], a few have also focused on the induction of protective cellular immunity against viruses [19-21].

Their capacity to transduce non-dividing dendritic cells (DCs) with high efficiency, ex-vivo [12, 14, 15, 19] as well as in vivo [13, 18, 22], accounts for their ability to elicit strong CTL responses.

Indeed, reports using lentiviral vectors to stimulate anti-tumor immunity show very promising results. Human DCs transduced by lentiviral vectors expressing tumor antigens stimulate specific CTL responses in vitro [12, 14, 15, 18]. In mice, the injection of lentiviral vector particles or lentiviral vector transduced DCs induce strong and specific anti-tumor cellular immune responses [13, 15, 18] and confer protection from tumor challenge [12, 17]. These responses are more potent than the ones obtained by classical immunization with peptide plus adjuvant [13] or even peptide-pulsed antigen presenting cells (APCs) whether assayed ex vivo [20] or in vivo [16, 21]. The observed advantage could be due to the continuous presentation of the antigen in vector-transduced APCs in contrast to the transient antigen presentation that ensues from peptide pulsing of APCs [16, 20].

To date, little is known of the ability of lentiviral vectors to stimulate an antibody-based protective immunity. Nevertheless, their high transduction efficiency could also grant them a strong ability to induce humoral immunity. Moreover, their seemingly preferential tropism for DCs when injected in vivo [13, 18, 22] could further enhance their capacity to elicit a protective antibody-based immunity, since DCs are powerful stimulators of CD4 T cells, which are needed for the correct development of a B-cell based immune response. Furthermore, in a vaccination scenario, the stable expression of the antigen from transduced cells might preclude the need for several injections.

Indeed, it is widely accepted that the humoral immune response is the essential component of protective immunity against West Nile Virus (WNV) [23-25]. The envelope E-glycoprotein from WNV, which possesses neutralizing epitopes [26], elicits protective immune responses when injected as a recombinant antigen [27] or expressed either by naked DNA [28] or a replicative measles vector [29]. The fact that passive transfer of neutralizing antibodies to the soluble form of the envelope E glycoprotein (sE) from WNV strain IS-98-ST1 protected mice from WNV encephalitis further demonstrates that the humoral response is sufficient for protection against WNV challenge [29].

WNV is a mosquito-borne flavivirus in the Japanese encephalitis serocomplex of the Flaviviridae family. It is transmitted in natural cycles between birds and mosquitoes, but it can infect many species of mammals [30]. Zoonotic WNV recently became a major health concern in North America, the Middle East, and Europe, due to the emergence of a more virulent strain in Israel in 1998 and then in New York in 1999 (Isr98/NY99). Severe clinical manifestations of WNV infection essentially involve the central nervous system and can cause significant mortality in humans and in a large range of animal species, particularly horses and birds (for review see [30]). As a consequence, an urgent demand exists for the development of an efficient vaccine that can provide quick, strong and long lasting immunity.

SUMMARY OF THE INVENTION

This invention aids in fulfilling these needs in the art. This invention relates to the potential of lentiviral vectors to elicit a humoral immune response. Whether immunization with a lentiviral-based vaccine could protect against West Nile Virus (WNV) infection was investigated. It was surprisingly discovered that lentiviral vectors can elicit antibody based protective immunity.

In the present invention, the potential of a lentiviral vector-based vaccine was evaluated to elicit humoral immunity against West Nile Virus (WNV), a mosquito-borne flavivirus that causes encephalitis in humans, birds and horses. Remarkably, a single immunization with a minute dose of TRIP/$sE_{WNV}$, a lentiviral vector expressing the secreted soluble form of the envelope E-glycoprotein ($sE_{WNV}$) from the highly virulent IS-98-ST1 strain of WNV, induced a specific humoral response and protection against WNV infection in a mouse model of WNV encephalitis. This single immunization elicited a long-lasting, protective and sterilizing humoral immunity, only one week after priming. These results demonstrate the applicability of lentiviral vectors as efficient non-replicating vaccines against pathogens for which a neutralizing humoral response is actively required for protective immunity. TRIP/$sE_{WNV}$ lentiviral vector appears as a promising tool for veterinary vaccination against zoonotic WNV.

Thus, this invention provides a method of producing antibodies in vivo comprising administration of a lentiviral vector to an animal, wherein the lentivirus comprises a heterologous nucleic acid encoding an antigen, and wherein the antigen elicits a humoral response in the animal. The invention encompasses a lentiviral vector that induces protective immunity to an animal in need thereof, including, for example, long-lasting protective immunity and sterilizing immunity. In one embodiment, the animal in need thereof is selected from humans; horses; birds; poultry; pigs; cattle, including bovines, ovins, and caprins; rodents, including hamsters, rats, and mice; pets; and reptiles.

This invention additionally provides a method of producing antibodies in vivo comprising administration of a lentiviral vector to an animal, wherein the lentivirus comprises a heterologous nucleic acid encoding an antigen, and wherein the antigen elicits a humoral response in the animal, wherein the lentiviral vector induces protective immunity against an infectious microorganism In one embodiment, the infectious microorganism is West Nile Virus. In another embodiment, the lentiviral vector comprises a nucleic acid encoding a peptide or polypeptide bearing at least a B epitope. The polypeptide bearing at least a B epitope can be, for example, a microorganism membrane protein or a fragment thereof, and in particular envelope E-glycoprotein from West Nile Virus, or a fragment thereof. The lentiviral vector may comprise a carboxyl terminal-truncated E glycoprotein from West Nile Virus lacking the transmembrane anchoring region, for example, a carboxyl terminal-truncated E glycoprotein comprising residues 1-441 of the envelope E-glycoprotein from West Nile Virus strain IS-98-ST1. In another embodiment, the heterologous nucleic acid encodes a variant of envelope E-glycoprotein from West Nile Virus. The invention encompasses a variant heterologous nucleic acid that hybridizes under conditions of stringent hybridization, which are described hereinafter, to a nucleic acid from West Nile Virus strain IS-98-ST1 encoding envelope E-glycoprotein.

The invention also provides for a method for vaccinating an animal against West Nile Virus infection, comprising administering to an animal in need thereof, one or more times, a lentiviral vector comprising a nucleic acid encoding a peptide bearing at least a B epitope. The peptide bearing at least a B epitope can be, for example, a microorganism membrane protein or a fragment thereof, and in particular envelope E-glycoprotein from West Nile Virus, or a fragment thereof, with an acceptable physiological carrier and/or an adjuvant. In vivo suitable routes of administration include, for example, an intraperitoneal route, intravenous route, intramuscular route, oral route, mucosal route, sublingual route, intranasal route, subcutaneous route or intradermic route. Ex vivo suitable routes include administration of autologous cells transduced with the lentiviral vector [i.e. Antigen Presenting Cells (APC) as dendritic cells (DC) or B cells]. In one embodiment, the heterologous nucleic acid encodes a peptide or polypeptide bearing at least a B epitope. In a preferred embodiment, the polypeptide encodes a membrane protein or a fragment thereof. In another preferred embodiment, the heterologous nucleic acid encodes carboxyl terminal-truncated E glycoprotein from West Nile Virus lacking the transmembrane anchoring region. In another, the carboxyl terminal-truncated E glycoprotein comprises residues 1-441 of the envelope E-glycoprotein from West Nile Virus strain IS-98-ST1. A preferred embodiment of this invention encompasses administering the lentiviral vector in a limited number of doses, such as, for example, a single dose or two or three doses. In one embodiment, this dose comprises, for example, vector particles equivalent to 0.5 ng to 5000 ng of p24 antigen. In mice, the preferred dose can vary from 0.5 ng to 50 ng, while in horses the preferred dose can vary from 50 ng to 500 ng. The invention encompasses the treatment of such animals, for example, as humans; horses; birds; poultry; pigs; cattle, including bovines, ovins, and caprins; rodents, including hamsters, rats, and mice; pets; and reptiles.

The invention also provides for a method for vaccinating an animal against microorganism infection, comprising administering to an animal in need thereof, one or more times, a lentiviral vector comprising a heterologous nucleic acid encoding an immunogenic membrane protein or a fragment thereof of such microorganism. As used herein, the term microorganism encompasses viruses, bacteria, and parasites.

In a preferred embodiment the invention provides a method for vaccinating an animal in need thereof against virus infection, such as a flavivirus infection, and in particular a method for vaccinating an animal in need thereof against West Nile Virus infection by administering a lentiviral vector comprising a variant of envelope E-glycoprotein from West Nile Virus, or a fragment thereof, with an acceptable physiological carrier and/or an adjuvant. The invention encompasses such a method of vaccination wherein the heterologous nucleic acid hybridizes under conditions of stringent hybridization to a nucleic acid from West Nile Virus strain IS-98-ST1 encoding envelope E-glycoprotein. In one embodiment, the lentiviral vector is administered one time, for example, in a dose of vector particles equivalent to 0.5 ng to 5000 ng of p24 antigen. The animal in need thereof can include, for example, humans; horses; birds; poultry; pigs; cattle, including bovines, ovines, and caprines; rodents, including hamsters, rats, and mice; pets, such as cats and dogs; and reptiles.

The invention also provides for an immunogenic composition comprising a lentiviral vector, wherein the lentiviral vector comprises a heterologous nucleic acid encoding an antigen in an amount sufficient to induce an immunogenic or protective response in vivo, and a pharmaceutically acceptable carrier therefor. The invention encompasses an immunogenic composition, wherein the heterologous nucleic acid encodes a peptide bearing at least a B epitope. A peptide bearing at least a B epitope can be, for example, a microorganism membrane protein or a fragment thereof, and in particular envelope E-glycoprotein from West Nile Virus, or a fragment thereof, or a carboxyl terminal-truncated E-glycoprotein from West Nile Virus lacking the transmembrane anchoring region. In one embodiment, the carboxyl terminal-truncated E glycoprotein comprises residues 1-441 of the envelope E-glycoprotein from West Nile Virus strain IS-98-ST1.

The invention also provides for an immunogenic composition comprising a lentiviral vector, wherein the lentiviral vector comprises a heterologous nucleic acid encoding an antigen in an amount sufficient to induce an immunogenic or protective response in vivo, and a pharmaceutically acceptable carrier therefor, and wherein the heterologous nucleic acid encodes a variant of envelope E-glycoprotein from West Nile Virus. In one example, the heterologous nucleic acid hybridizes under conditions of stringent hybridization to a nucleic acid from West Nile Virus strain IS-98-ST1 encoding envelope E-glycoprotein.

The invention encompasses a lentiviral vector that directs the expression of a heterologous nucleic acid, wherein the vector comprises cytomegalovirus immediate early promoter, and wherein the heterologous nucleic acid encodes envelope E-glycoprotein from West Nile Virus, or a fragment thereof. The heterologous nucleic acid can encode, for example, carboxyl terminal-truncated E-glycoprotein from West Nile Virus lacking the transmembrane anchoring region. In one embodiment, the carboxyl terminal-truncated E-glycoprotein comprises residues 1-441 of envelope E-glycoprotein from West Nile Virus strain IS-98-ST1. The invention also provides for a substantially purified host cell transfected or transduced with such a lentiviral vector, and for a method for the production of envelope E-glycoprotein polypeptide from West Nile Virus, or a fragment thereof, comprising culturing a host cell transfected or transduced with such a lentiviral vector under conditions promoting expression, and recovering the polypeptide from the host cell or the culture medium.

The invention further provides for a lentiviral vector that directs the expression of a heterologous nucleic acid, wherein the vector comprises cytomegalovirus immediate early promoter, and wherein the heterologous nucleic acid encodes a variant of envelope E-glycoprotein from West Nile Virus. In one embodiment, the heterologous nucleic acid hybridizes under conditions of stringent hybridization to a nucleic acid from West Nile Virus strain IS-98-ST1 encoding envelope E-glycoprotein. The invention encompasses a substantially purified host cell transfected or transduced with such a lentiviral vector, and for a method for the production of a variant of envelope E-glycoprotein from West Nile Virus comprising culturing a host cell transfected or transduced with such a lentiviral vector under conditions promoting expression, and recovering the polypeptide from the host cell or the culture medium.

The invention further provides for a lentiviral vector that directs the expression of a heterologous nucleic acid, wherein the vector comprises cytomegalovirus immediate early promoter, and wherein the heterologous nucleic acid comprises green fluorescent protein. The invention also encompasses a substantially purified host cell transfected or transduced with this lentiviral vector.

The invention encompasses a method of vaccinating against a pathogenic agent comprising administering a lentiviral vector to an animal in need thereof, wherein the lentiviral vector comprises a heterologous nucleic acid encoding an antigen, and wherein the antigen elicits antibodies against the pathogenic agent. The invention encompasses, for example, a method of vaccinating wherein administration of the lentiviral vector elicits long-lasting humoral immunity. The invention also encompasses, for example, a method of vaccinating wherein administration of the lentiviral vector elicits neutralizing antibodies against the pathogenic agent. The animal in need thereof can include, for example, humans; horses; birds; poultry; pigs; cattle, including bovines, ovines, and caprines; rodents, including hamsters, rats, and mice; pets, such as cats and dogs; and reptiles. In one embodiment, the lentiviral vector comprises a nucleic acid encoding envelope E-glycoprotein from West Nile Virus, or a fragment thereof, and the pathogenic agent is West Nile Virus. In another embodiment, the envelope E-glycoprotein from West Nile Virus lacks a transmembrane anchoring region. In another, the administration of lentiviral vector comprises at least one dose of vector particles equivalent to 0.5 ng to 5000 ng of p24 antigen.

The invention also provides for a method of delivering DNA for producing antibodies in vivo comprising administration of a lentiviral vector to an animal, wherein the lentiviral vector comprises a heterologous nucleic acid encoding an antigen, and wherein the antigen elicits a humoral response in the animal. The invention encompasses a lentiviral vector that induces protective humoral immunity to an animal in need thereof. In one embodiment, the animal in need thereof is selected from humans; horses; birds; poultry; pigs; cattle, including bovines, ovins, and caprins; rodents, including hamsters, rats, and mice; pets; and reptiles.

This invention additionally provides for a method of delivering DNA for producing antibodies in vivo comprising administration of a lentiviral vector to an animal, wherein the lentiviral vector comprises a heterologous nucleic acid encoding an antigen, and wherein the antigen elicits a humoral response in the animal, wherein the lentiviral vector induces protective immunity against West Nile Virus. In one embodiment, the lentiviral vector may comprise a nucleic acid encoding an envelope E-glycoprotein from West Nile Virus, or a fragment thereof. The lentiviral vector may comprise a nucleic acid encoding a carboxyl terminal-truncated E glycoprotein from West Nile Virus lacking the transmembrane anchoring region, for example, a carboxyl terminal-truncated E glycoprotein comprising residues 1-441 of the envelope E-glycoprotein from West Nile Virus strain IS-98-ST1. In another embodiment, the heterologous nucleic acid encodes a variant of envelope E-glycoprotein from West Nile Virus. The invention encompasses a variant heterologous nucleic acid that hybridizes under conditions of stringent hybridization, which are described hereinafter, to a nucleic acid from West Nile Virus strain IS-98-ST1 encoding envelope E-glycoprotein.

The invention also encompasses a method comprising administration of a lentiviral vector to an animal, wherein the lentiviral vector comprises a heterologous nucleic acid encoding an antigen, and wherein the antigen elicits a humoral response in the animal. The invention encompasses a lentiviral vector that induces protective humoral immunity to an animal in need thereof. In one embodiment, the animal in need thereof is selected from humans; horses; birds; poultry; pigs; cattle, including bovines, ovins, and caprins; rodents, including hamsters, rats, and mice; pets; and reptiles.

The invention additionally provides for a method comprising administration of a lentiviral vector to an animal, wherein the lentiviral vector comprises a heterologous nucleic acid encoding an antigen, wherein the antigen elicits a humoral response in the animal, and wherein the antigen expressed in the animal after their transduction with the lentiviral vector induces protective immunity against an infectious microorganism, such as, for example, West Nile Virus. In one embodiment, the lentiviral vector comprises a nucleic acid encoding a membrane protein from an infectious microorganism (in particular encoding an envelop protein and more preferentially, the envelope E-glycoprotein from West Nile Virus, or a fragment thereof. The lentiviral vector may comprise a nucleic acid encoding the carboxyl terminal-truncated E glycoprotein from West Nile Virus lacking the transmembrane anchoring region, for example, a carboxyl terminal-truncated E glycoprotein comprising residues 1-441 of the envelope E-glycoprotein from West Nile Virus strain IS-98-ST1. In another embodiment, the heterologous nucleic acid encodes a variant of envelope E-glycoprotein from West Nile Virus. In one embodiment, the invention encompasses a heterologous nucleic acid that hybridizes under conditions of stringent hybridization to those described hereinafter, for example, to a nucleic acid from West Nile Virus strain IS-98-ST1 encoding envelope E-glycoprotein.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

BRIEF DESCRIPTION OF THE DRAWINGS

FIG. 2 shows the detection of anti-E$_{WNV}$ antibodies in sera from TRIP/sE$_{WNV}$ vaccinated mice Vero cells were infected with WNV strain IS-98-ST1 (WNV) or mock-infected (No virus). Radio-labeled cell lysates were immunoprecipitated with pooled immune sera (dilution 1:100). Samples were analyzed by SDS-15% PAGE under non-reducing conditions. (A) Sera from TRIP/sE$_{WNV}$ immunized mice collected at day 6, 13, 20 and 27 post-immunization (p.i). (B) Sera from resistant congenic BALB/c-MBT mice inoculated with WNV (sera to WNV). Antisera to lymphochoriomeningitis virus (LCMV) were used as a negative control. WNV structural glycoproteins C, prM and E and non-structural proteins NS3 and NS2A are shown. (C) Sera from TRIP/sE$_{WNV}$ immunized mice collected 21 days after WNV challenge, which was performed 7 or 14 days post-immunization. As a positive control, viral antigens were immunoprecipitated with anti-WNV HMAF.

FIG. 3 shows that heat-inactivation of TRIP/sE$_{WNV}$ vector particles abolishes transduction. 293T cells were transduced with a TRIP/GFP vector (66 ng of p24 antigen per ml), heat-inactivated (70° C. for 10 min) or not. At 48 h post-transduction, GFP expression was detected by FACS.

FIG. 4 shows the nucleic acid sequence (SEQ ID NO:9) of the secreted form of the West Nile Virus E-glycoprotein from strain IS-98-ST1, with start and stop codons added at the ends of the sequence.

FIG. 5 shows the nucleic acid sequence (SEQ ID NO:10) of the secreted form of the West Nile Virus E-glycoprotein from strain IS-98-ST1.

FIG. 6 shows the amino acid sequence (SEQ ID NO:11) of the secreted form of the West Nile Virus E-glycoprotein from strain IS-98-ST1. The signal sequence at the N-terminus is underlined.

FIG. 7 shows the amino acid sequence of Domain III (SEQ ID NO:12) from West Nile Virus E-glycoprotein from strain IS-98-ST1.

FIG. 8 shows the complete nucleic acid sequence of the lentiviral vector pTRIPsE$_{WNV}$ (SEQ ID NO:13) bearing the heterologous sequence of truncated West Nile Virus E-glycoprotein from West Nile Virus strain IS-98-ST1.

DETAILED DESCRIPTION

Figure 1:
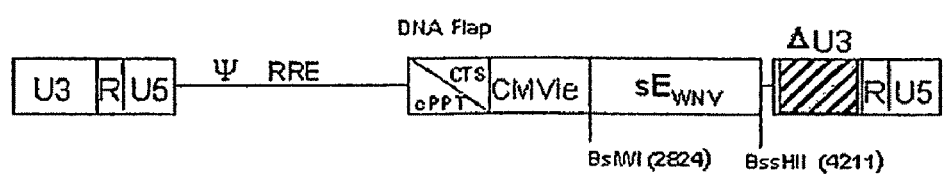
FIG. 1 shows the Expression of $sE_{WNV}$ in 293T cells transduced with TRIP/$sE_{WNV}$. (A) Schematic representation of the TRIP/$sE_{WNV}$ vector. The IS-98-ST1 cDNA coding for $sE_{WNV}$ was subcloned from the TOPO/$sE_{WNV}$ plasmid [29] into the TRIP lentiviral vector between the BsiW1 and BssHII cloning sites and under the control of the human cytomegalovirus immediate early promoter (CMVie). LTR=Long Terminal Repeat. (B) Detection of sE$_{WNV}$ protein in TRIP/sE$_{WNV}$ transduced 293T cells. 293T cells were transduced with the amount of TRIP/sE$_{WNV}$ vector particles equivalent of 100 ng/ml of p24 antigen (left), or left untransduced (right). At 48 hours post-transduction, 293T cells were immunostained with an anti-WNV HMAF (Hyperimmune Mouse Ascitic Fluid).
Figure 1:
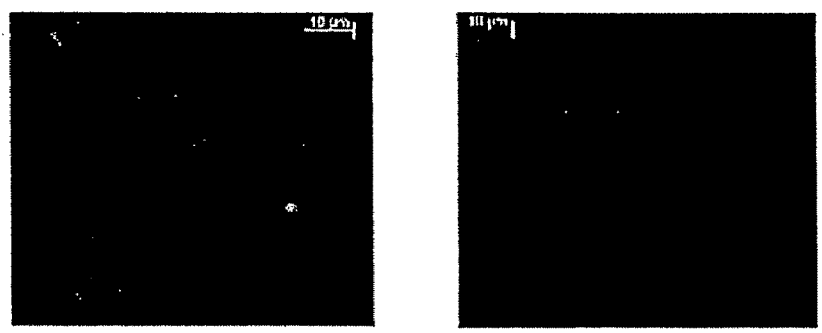

Lentiviral vectors for inducing protective humoral responses have been discovered. In one embodiment, the lentiviral vectors are replication-defective retroviral vectors comprising cis-active sequences necessary for reverse transcription (PPT 3', PBS and R regions of the LTRs), nuclear import (cPPT-CTS), and integration (psi), and a heterologous nucleic acid encoding an antigen. In this embodiment, structural and enzymatic proteins are provided in "trans." The lentiviral vectors can comprise integration repeat (IR) sequences and Tips of the LTR, as well as transcriptional sequences as ORF and promoters. The lentiviral vector particle can be pseudotyped by any viral or non-viral envelope to facilitate its entry into the target cell. One preferred site on the lentiviral vector for insertion of the heterologous nucleic acid is between the two LTRs, as explained below. Alternately, the heterologous nucleic acid can be, for example, inserted into the U3 or U5 regions of the LTRs, or provided as a replacement for the U3 or U5 regions of the LTRs.

In one embodiment, the lentiviral vector comprises a heterologous nucleic acid encoding a peptide bearing at least one B epitope. In preferred embodiments, the heterologous nucleic acid encodes a membrane protein from an infectious microorganism, such as, for example, an envelope protein. In one preferred embodiment, the heterologous nucleic acid encodes envelope E-glycoprotein from West Nile Virus, or a fragment thereof.

The term "lentiviral vector" means that the vector contains a polynucleotide sequence that: (1) is not associated with all or a portion of a polynucleotide with which it is associated in nature, (2) is linked to a polynucleotide other than that to which it is linked in nature, or (3) does not occur in nature. Lentiviral vectors of the invention encompass vectors derived from, for example, HIV-1, HIV-2, SIV (simian immunodeficiency virus), EIAV (equine infectious anaemia virus), FIV (feline immunodeficiency virus), CAEV (Caprine arthritis encephalitis virus), and VMV (Visna/maedi virus). Lentiviral vectors also encompass chimeric lentiviruses derived from at least two different lentiviruses.

The terms "polypeptide" and "protein", used interchangeably herein, refer to a polymeric form of amino acids of any length, and includes chemically or biochemically modified or derivatized amino acids, as well as polypeptides having modified peptide backbones. The term includes fusion proteins, such as GST fusion proteins and pegylated proteins, fusion proteins with a heterologous amino acid sequence, fusions with heterologous or homologous leader sequences, with or without N-terminal methionine residues; immunologically tagged proteins; and the like.

A "fragment" of a polypeptide sequence refers to a polypeptide sequence that is shorter than the reference sequence but that retains a biological function or activity which is recognized to be the same as the reference polypeptide. Such an activity may include, for example, the ability to stimulate an immune response. A fragment retains at least one epitope of the reference polypeptide.

The term "purified" as used herein, means that a polypeptide that is essentially free of association with other proteins or polypeptides, for example, as a purification product of recombinant host cell culture or as a purified product from a non-recombinant source. The term "substantially purified", as used herein, refers to a mixture that contains a polypeptide and is essentially free of association with other proteins or polypeptides, but for the presence of known proteins that can be removed using a specific antibody, and which substantially purified polypeptides can be used as an antigen.

The term "antigen" as used herein, means a substance capable of stimulating an immune response. Preferred antigens encompass at least one B-epitope, wherein a B-epitope is capable of eliciting a humoral immune response. Such preferred antigens include, for example, surface antigens, such as envelope or other membrane proteins, and fragments thereof.

The term "pathogen" as used herein, means a specific causative agent of disease, and may include, for example, any bacteria, virus or parasite.

The term "disease" as used herein, means an interruption, cessation, or disorder of body function, system, or organ. Preferred diseases include infectious diseases.

The term "humoral immunity" as used herein, means antibodies elicited by an antigen, and all the accessory processes that accompany it.

The term "protective humoral immunity" as used herein, means a humoral immune response that confers the essential component of protection against a pathogen.

The term "sterilizing humoral immunity" as used herein, means a humoral immune response that prevents the establishment of any detectable infection by a pathogen.

The term "long-lasting humoral immunity" as used herein, means that some aspect of humoral immunity is detectable three months after antigen administration, such as, for example, antibodies elicited by the antigen. Suitable methods of antibody detection include, but are not limited to, such methods as ELISA, immunofluorescence (IFA), focus reduction neutralization tests (FRNT), immunoprecipitation, and Western blotting.

The term "neutralizing humoral response" as used herein, means that the antibodies elicited during humoral immunity directly block the ability of a pathogen to infect cells.

The term "quick response" as used herein, means that protective humoral immunity is conferred within three weeks of antigen administration. The term "very quick response" as used herein, means that protective humoral immunity is conferred within one week of antigen administration.

Hybridization reactions can be performed under conditions of different "stringency." Conditions that increase stringency of a hybridization reaction are known in the art. For example, stringent conditions for both DNA/DNA and DNA/RNA hybridization are described in Sambrook and Russell, *Molecular Cloning, A Laboratory Manual*, 3$^{rd}$ Ed., Cold Spring Harbor Laboratory Press, Cold Spring Harbor, N.Y., 2001. Moreover, a person skilled in the art would know how to modify the conditions as necessary for the degree of stringency required for a particular hybridization.

Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where 1×SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water.

An example of stringent hybridization conditions is hybridization at 50° C. and 0.1×SSC (15 mM sodium chloride/1.5 mM sodium citrate). Another example of stringent hybridization conditions is overnight incubation at 42° C. in a solution containing 50% formamide, 1×SSC (150 mM NaCl, 15 mM sodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C. A further example of high stringency conditions includes aqueous hybridization (e.g., free of formamide) in 6×SSC (where 20×SSC contains 3.0 M NaCl and 0.3 M sodium citrate), 1% sodium dodecyl sulfate (SDS) at 65° C. for about 8 hours (or more), followed by one or more washes in 0.2×SSC, 0.1% SDS at 65° C.

A "variant" polypeptide as referred to herein means a polypeptide substantially homologous to the reference polypeptide, but which has an amino acid sequence different from that of reference polypeptides because of one or more deletions, insertions, or substitutions. The variant amino acid sequence preferably is at least 90% identical to the reference polypeptide, and most preferably at least 95% identical. The percent identity can be determined, for example by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap; and (3) no penalty for end gaps.

Variants can comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring polypeptide variants are also encompassed by the invention. Examples of such variants are proteins that result from alternate mRNA splicing events or from proteolytic cleavage of the polypeptides. Variations attributable to proteolysis include, for example, differences in the termini upon expression in different types of host cells, due to proteolytic removal of one or more terminal amino acids from the polypeptides. Variations attributable to frameshifting include, for example, differences in the termini upon expression in different types of host cells due to different amino acids.

The term "binds specifically," in the context of antibody binding, refers to high avidity and/or high affinity binding of an antibody to a specific polypeptide, or more accurately, to a specific epitope of a specific polypeptide. Antibody binding to such epitope is typically stronger than binding of the same antibody to any other epitope or any other polypeptide which does not comprise the epitope. Such an antibody is typically produced by injecting the specific polypeptide into an animal to elicit the production of antibodies. Such an antibody may be capable of binding other polypeptides at a weak, yet detectable, level (e.g., 10% or less of the binding shown to the polypeptide of interest). Such weak binding, or background binding, is readily discernible from the specific antibody binding, for example, by use of appropriate controls. In general, antibodies of the invention specifically bind to a specific polypeptide with a binding affinity of $10^{-7}$ M or more, preferably $10^{-8}$ M or more (e.g., $10^{-9}$ M, $10^{-10}$, $10^{-11}$, etc.).

A "pharmaceutically acceptable carrier" refers to a non-toxic solid, semisolid or liquid filler, diluent, encapsulating material or formulation auxiliary of any conventional type. A "pharmaceutically acceptable carrier" is non-toxic to recipients at the dosages and concentrations employed and is compatible with other ingredients of the formulation. For example, the carrier for a formulation containing polypeptides preferably does not include oxidizing agents and other compounds that are known to be deleterious to polypeptides. Suitable carriers include, but are not limited to, water, dextrose, glycerol, saline, ethanol, and combinations thereof. The carrier may contain additional agents such as wetting or emulsifying agents, pH buffering agents, or adjuvants which enhance the effectiveness of the formulation. Topical carriers include liquid petrolatum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents may be added as necessary. Percutaneous penetration enhancers such as Azone may also be included.

The complete genome sequence of West Nile Virus strain IS-98-ST1 (or STD) is available on GenBank accession number AF 481864 (GI: 19387527, version of May 21, 2002).

The invention provides for isolated and purified, or homogeneous, envelope E-glycoprotein polypeptides from West Nile Virus, both recombinant and non-recombinant. Variants and derivatives of native envelope E-glycoprotein polypeptides that can be used as antigens can be obtained by mutations of nucleotide sequences coding for native envelope E-glycoprotein polypeptides. Alterations of the native amino acid sequence can be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion, or insertion. Exemplary methods of making the alterations set forth above are disclosed by Walder et al. (*Gene* 42:133, 1986); Bauer et al. (*Gene* 37:73, 1985); Craik (*BioTechniques*, January 1985, 12-19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462, all of which are incorporated by reference.

Within an aspect of the invention, the lentiviral vector can be utilized to prepare antibodies that specifically bind to polypeptides. The term "antibodies" is meant to include polyclonal antibodies, monoclonal antibodies, fragments thereof such as F(ab')2 and Fab fragments, as well as any recombinantly produced binding partners. Antibodies are defined to be specifically binding if they bind envelope E-glycoprotein polypeptides with a $K_a$ of greater than or equal to about $10^7$ $M^{-1}$. Affinities of binding partners or antibodies can be readily determined using conventional techniques, for example, those described by Scatchard et al., *Ann. N.Y Acad. Sci.*, 51:660 (1949). Polyclonal antibodies can be readily generated from a variety of sources, for example, horses, cows, goats, sheep, dogs, chickens, rabbits, mice, or rats, using procedures that are well known in the art.

Recombinant expression vectors containing can be prepared using well known methods. For a review of molecular biology techniques see Sambrook and Russell, *Molecular Cloning: A Laboratory Manual*, CSHL Press 2001, 3$^{rd}$ Ed. The expression vectors can include an insert sequence, such as West Nile Virus envelope E-glycoprotein sequence, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are "operably linked" when the regulatory sequence functionally relates to the insert sequence. Thus, a promoter nucleotide sequence is operably linked to a envelope E-glycoprotein sequence if the promoter nucleotide sequence controls the transcription of the envelope E-glycoprotein DNA sequence. The ability to replicate in the desired host cells, usually conferred by an origin of replication, and a selection gene by which transformants are identified can additionally be incorporated into the expression vector.

In addition, sequences encoding appropriate signal peptides that are not naturally associated with the insert sequence can be incorporated into expression vectors.

Suitable host cells for expression include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, New York, (1985).

Once the lentiviral vector of the invention have been obtained, they can be used to produce polyclonal and monoclonal antibodies. Thus, a protein or polypeptide expressed in vivo or ex vivo by means of the lentiviral vector of the invention can be used to immunize an animal host by techniques known in the art. Such techniques usually involve inoculation, but they may involve other modes of administration. A sufficient amount of the lentiviral vector is administered to create an immunogenic response in the animal host. Any host that can be infected by lentivirus can be used. Once the animal has been immunized and sufficient time has passed for it to begin producing antibodies to the antigen, polyclonal antibodies can be recovered. The general method comprises removing blood from the animal and separating the serum from the blood. The serum, which contains antibodies to the antigen, can be used as an antiserum to the antigen. Alternatively, the antibodies can be recovered from the serum. Affinity purification is a preferred technique for recovering purified polyclonal antibodies to the antigen, from the serum.

Monoclonal antibodies to the antigens of the invention can also be prepared. One method for producing monoclonal antibodies reactive with the antigens comprises the steps of infecting the host with the lentiviral vector; recovering antibody producing cells from the spleen of the host; fusing the antibody producing cells with myeloma cells deficient in the enzyme hypoxanthine-guanine phosphoribosyl transferase to form hybridomas; selecting at least one of the hybridomas by growth in a medium comprising hypoxanthine, aminopterin, and thymidine; identifying at least one of the hybridomas that produces an antibody to the antigen, culturing the identified hybridoma to produce antibody in a recoverable quantity; and recovering the antibodies produced by the cultured hybridoma.

These polyclonal or monoclonal antibodies can be used in a variety of applications. Among these is the neutralization of corresponding proteins. They can also be used to detect viral antigens in biological preparations or in purifying corresponding proteins, glycoproteins, or mixtures thereof, for example when used in an affinity chromatographic columns.

The envelope E-glycoprotein polypeptides can be used as antigens to identify antibodies to West Nile Virus in materials and to determine the concentration of the antibodies in those materials. Thus, the antigens can be used for qualitative or quantitative determination of the virus in a material. Such materials include animal tissue and animal cells, as well as biological fluids, such as animal body fluids, including animal sera. When used as a reagent in an immunoassay for determining the presence or concentration of the antibodies to West Nile Virus, the antigens provide an assay that is convenient, rapid, sensitive, and specific.

More particularly, the antigens can be employed for the detection of microorganism pathogen infection (in particular West Nile Virus) by means of immunoassays that are well known for use in detecting or quantifying humoral components in fluids. Thus, antigen-antibody interactions can be directly observed or determined by secondary reactions, such as precipitation or agglutination. In addition, immunoelectrophoresis techniques can also be employed. For example, the classic combination of electrophoresis in agar followed by reaction with anti-serum can be utilized, as well as two-dimensional electrophoresis, rocket electrophoresis, and immunolabeling of polyacrylamide gel patterns (Western Blot or immunoblot). Other immunoassays in which the antigens of the present invention can be employed include, but are not limited to, radioimmunoassay, competitive immunoprecipitation assay, enzyme immunoassay, and immunofluorescence assay. It will be understood that turbidimetric, colorimetric, and nephelometric techniques can be employed. An immunoassay based on Western Blot technique is preferred.

Immunoassays can be carried out by immobilizing one of the immunoreagents on a carrier surface while retaining immunoreactivity of the reagent. The reciprocal immunoreagent can be unlabeled or labeled in such a manner that immunoreactivity is also retained. These techniques are especially suitable for use in enzyme immunoassays, such as enzyme linked immunosorbent assay (ELISA) and competitive inhibition enzyme immunoassay (CIEIA).

When either of the immunoreagents are attached to a solid support, the support is usually a glass or plastic material. Plastic materials molded in the form of plates, tubes, beads, or disks are preferred. Examples of suitable plastic materials are polystyrene and polyvinyl chloride. If the immunoreagent does not readily bind to the solid support, a carrier material can be interposed between the reagent and the support. Examples of suitable carrier materials are proteins, such as bovine serum albumin, or chemical reagents, such as glutaraldehyde or urea. Coating of the solid phase can be carried out using conventional techniques.

The invention provides immunogenic lentiviral vector, and more particularly, protective lentiviral vector for eliciting a protective response against West Nile Virus. These lentiviral vectors can thus be employed as viral vaccines by administering the lentiviral vector to an animal susceptible to a pathogenic microorganism (a bacteria, a virus, a parasite) and are useful in preventing infection. In one embodiment, the lentiviral vectors of the invention comprise a heterologous nucleic acid encoding a membrane protein from flavivirus, for example, from West Nile Virus, and are useful to prevent infections, for example, from West Nile Virus infection. Conventional modes of administration can be employed. For example, administration can be carried out by oral, respiratory, parenteral routes, sublingual route, intranasal route, subcutaneous route or intradermic route.

The vaccine compositions of the invention are administered in a manner compatible with the dosage formulation, and in such amount as will be therapeutically effective and immunogenic. The quantity to be administered depends on the subject to be treated including, e.g., the capacity of the individual's immune system to induce an immune response.

The immunization schedule will depend upon several factors, such as the susceptibility of the host to infection, the weight of the host, and the age of the host. A single dose of the vaccine of the invention can be administered to the host or a primary course of immunization can be followed in which several doses at intervals of time are administered. Subsequent doses used as boosters can be administered as needed following the primary course.

An immunogenic response can be obtained by administering the lentiviral vector of the invention to the host in an amount of about 10 to about 500 micrograms antigen per kilogram of body weight, preferably about 50 to about 100 micrograms antigen per kilogram of body weight. The proteins and vaccines of the invention can be administered together with a physiologically acceptable carrier. For example, a diluent, such as water or a saline solution, can be employed.

To further achieve the objects and in accordance with the purposes of the present invention, a kit capable of diagnosing a West Nile Virus infection is described. This kit, in one embodiment, contains the antibodies of this invention, which are capable of binding to West Nile Virus envelope E-glycoprotein. This kit, in another embodiment, contains the polypeptides of this invention, which are capable of detecting the presence or absence of antibodies, which bind to the envelope E-glycoprotein polypeptide.

This invention will be described in greater detail in the following Examples.

Example 1

Materials and Methods

Cell culture and virus preparations. Human 293T cells and African green monkey kidney Vero cells were grown in Dulbecco's modified Eagle medium (DMEM) Glutamax (GIBCO) supplemented with 10% or 5% heat-inactivated Fetal Calf Serum (FCS) respectively. WNV strain IS-98-ST1 (GenBank accession number AF 481864) [31], a closely related variant of NY99 strain [32-34], was propagated in mosquito Aedes pseudoscutellaris AP61 cell monolayers. Purification in sucrose gradients, and virus titration on AP61 cells by focus immunodetection assay (FIA) using anti-WNV Hyperimmune Mouse Ascitic Fluid (HMAF) were performed as previously described [29, 31, 35]. Infectivity titers were expressed as Focus Forming Units (FFU).

Lentiviral vector construction and production. The 1.4 kb cDNA coding for the carboxyl terminal-truncated E glycoprotein lacking the transmembrane-anchoring region (residues E-1 to E-441; referred to as $sE_{WNV}$) from WNV strain IS-98-ST1 is described elsewhere [29]. The $sE_{WNV}$ coding cDNA was already modified by PCR to be flanked on the open reading frame extremities by BsiWI and BssHII restriction endonucleases sites. The cDNA was digested with BsiWI and BssHII and then cloned into the unique BsiWI and BssHII sites of the pTRIP ΔU3 CMV plasmid. The resulting vector plasmid, pTRIP.ΔU3.CMV.sE$_{WNV}$ (hereafter referred to as pTRIP/sE$_{WNV}$), contains the IS-98-ST1 sE glycoprotein sequence under the control of the cytomegalovirus immediate early promoter (CMVie).

Vector particles were produced by transient calcium phosphate co-transfection of 293T cells with the vector plasmid pTRIP/sE$_{WNV}$, an encapsidation plasmid (p8.7, [36]) and a VSV-G envelope expression plasmid (pHCMV-G; [37]) as previously described [38]. Quantification of p24 antigen content of concentrated vector particles was done with a commercial HIV-1 p24 ELISA kit (Perkin Elmer LifeSciences).

Quantitative PCR. For detection of the U5-R sequences in the lentiviral vector, primers and probes used were as follows:

probes LTR-FL 5'-CACAACAGACGGGCACACACTACT-TGA-fluorescein-3' (SEQ ID NO:1), LTR-LC 5'-RED640-CACTCAAGGCAAGCTTTATTGAGGC-phosphorylated-3' (SEQ ID NO:2), primers AA55M 5'-GCTAGAGATTTTCCACACTGACTAA-3' (SEQ ID NO:3), M667 5'-GGCTAACTAGGGAACCCACTG-3' (SEQ ID NO:4)[39]. For detection of CD3, the sequences of primers and probes were as follows: Probes CD3-P1 5'-GGCTGAAGGTTAGGGATACCAATATTCCTGTCTC-fluorescein-3' (SEQ ID NO:5), CD3-P2 5'-RED705-CTAGT-GATGGGCTCTTCCCTTGAGCCCTTC-phosphorylated-3' (SEQ ID NO:6) and primers CD3-in-F 5'-GGCTATCATTCTTCTTCAAGGTA-3' (SEQ ID NO:7) and CD3-in-R 5'-CCTCTCTTCAGCCATTTAAGTA-3' (SEQ ID NO:8). Primers and probes were synthesized by Proligo (France). Genomic DNA from approximately $3.10^6$ lentiviral vector transduced 293T cells was isolated 48 h after transduction using QIAamp® DNA Blood Mini Kit (QIAGEN, GmbH, Hilden). For real-time PCR analysis, 5 μL of DNA were mixed with 15 μL of a PCR master mix consisting of 1× Jumpstart™ Taq ReadyMix™ (Sigma), 1.9 mM $MgCl_2$, 1.5 μM of forward and reverse primers (AA55MIM667 or CD3-in-F/CD3 in-R), 200 nM of the probes (LTR-FL/LTR-LC or CD3-P1/CD3-P2) and, 1.5 units of Taq DNA Polymerase (Invitrogen). Amplifications were performed on a LightCycler 2.0 (Roche Applied Science), using one cycle of 95° C. for 3 min, and 40 cycles of 95° C. for 5 s, 55° C. for 15 s and 72° C. for 10 s. To take into account the possible plasmid contamination of vector stocks, DNA from 293T cells transduced with heat-inactivated (10 min at 70° C.) vector was always tested in parallel. For negative controls 5 μL of genomic DNA from untransduced cells was used. Each DNA sample was tested in duplicate and the mean values are reported. Ten-fold serial dilutions of known concentration of the plasmid pTripCD3, containing the relevant sequences U5-R and CD3, were amplified in parallel with DNA samples to generate a standard curve.

The total number of vector copies per cell was calculated by normalizing the number of U5-R copies to the number of 293T cells, as quantified by the copy number of CD3 molecules on the same genomic DNA sample, and then subtracting the number of copies obtained for the heat-inactivated vector-transduced cells.

Mouse antisera to WNV. Anti-WNV Hyperimmune Mouse Ascitic Fluid (HMAF) was obtained by repeated immunization of adult mice with WNV strain IS-98-ST1 followed by the inoculation of sarcoma 180. The sera to WNV were obtained by immunization of adult WNV-resistant BALB/c-MBT congenic mice with $10^3$ FFU of IS-98-ST1 as described previously [31]. Mouse polyclonal anti-WNV antibodies were collected 1 month after inoculation.

Mice immunization and WNV challenge. All animal experiments were conducted in accordance with the guidelines of the Office Laboratory of Animal Care at the Pasteur Institute. Six to eight-week-old 129 mice were intraperitoneally (i.p.) inoculated with varying doses of TRIP/sE$_{WNV}$ vector particles in 0.1 ml Dulbecco's PBS (DPBS; pH 7.5) supplemented with buffered 0.2% bovine serum albumin (DPBS/0.2% BSA, Sigma). WNV challenge was performed by i.p. inoculation of neurovirulent WNV strain IS-98-ST1 (i.p. $LD_{50}$=10 FFU) as previously described [29, 31]. The challenged mice were monitored daily for signs of morbidity or mortality, for up to 21 days.

Measurement of serum antibody responses. Mice were bled via the periorbital route and sera were heat-inactivated for 30 min at 56° C. Anti-WNV antibodies were detected by ELISA using sucrose-purified WNV IS-98-ST1 as viral antigen [29, 31]. Peroxidase-conjugated anti-mouse immunoglobulin (H+L) (Jackson Immuno Research) at a 1:4,000 dilution, and peroxidase-conjugated anti-mouse IgM (μ-chain specific) or IgG (γ-chain specific) (Sigma) at a 1:20,000 dilution were used as secondary antibodies. The end point titer was calculated as the reciprocal of the last dilution eliciting twice the optical density (OD) of sera from TRIP/GFP inoculated mice that served as negative controls.

Anti-WNV neutralizing antibodies were detected by a focus reduction neutralization test (FRNT) on Vero cells as previously described [29]. The end-point titer was calculated as the reciprocal or the highest serum dilution tested that reduced the number of FFU by 90% ($FRNT_{90}$).

Radioimmunoprecipitation assay. Vero cells cultured on 25 $cm^2$ flask were infected with WNV strain IS-98-ST1 at a high multiplicity of infection. At 20 h post-infection, cells were starved for 1 h in DMEM depleted in methionine (ICN Biomedicals) and radiolabeled with 100 μCi/ml Trans$^{35}$S-Label™/ml (ICN Biomedicals) for 3 h. After three washes with cold PBS, cells were lysed with RIPA lysis buffer (50 mM Tris-Cl, 150 mM NaCl, 10 mM EDTA, 1% Triton X-100, 0.5% deoxycholate, 0.1% SDS, pH 8.0) supplemented with 25 μg/ml aprotinin (Sigma) for 10 min at 4° C. The cell lysates were then clarified by centrifugation at 10,000 rpm for 5 min at 4° C. Radioimmunoprecipitation (RIP) assay was performed as described previously [29, 40]. Viral antigens were immunoprecipitated with mouse anti-WNV antibodies. The samples were analyzed by SDS-15% PAGE under non-reducing conditions.

Indirect immunofluorescence and flow cytometry assays. For indirect immunofluorescence (IF) analysis, human 293T cells cultured on 8-chamber Glass-Labteks (Nunc) were transduced with TRIP/sE$_{WNV}$ vector particles. After 48 h, cells were fixed with 3% paraformaldehyde (PFA) in PBS for 20 min and permeabilized with 0.1% Triton X-100 in PBS for 4 min. Cells were incubated with anti-WNV HMAF at a 1:100 dilution in PBS for 1 h. After blocking with DPBS/0.2% BSA, cells were further incubated with a Cy3-conjugated anti-mouse IgG antibody (Amersham Pharmacia) at a 1:500 dilution in DPBS/0.2% BSA. Cell nuclei were visualized with DAPI. The slides were examined using a Zeiss Axioplan microscope with ApoTome system.

For flow cytometry analysis, 293T cells cultured on 25 $cm^2$ flasks were transduced with TRIP/GFP, either heat-inactivated (70° C. for 10 min) or not. At 48 h, cells were detached, washed and fixed with 2% PFA. The GFP fluorescence intensity was measured by FACS and analyzed with CellQuest software.

Example 2

Expression of the Secreted Form of the E Glycoprotein of WNV by the Recombinant Trip Lentiviral Vector To evaluate whether immunization with a lentiviral vector-based vaccine can protect against WNV encephalitis, a lentiviral vector was generated, TRIP/sE$_{WNV}$, which expresses a soluble form of the E glycoprotein from the WNV strain IS-98-ST1 (sE$_{WNV}$), under the control of the CMV immediate early promoter (CMV$_{i.e.}$) (FIG. 1A). We previously demonstrated the efficient secretion of sE$_{WNV}$ in the culture medium of cells infected by a recombinant measles vector [29]. Expression of sE$_{WNV}$ in lentiviral vector-transduced 293T cells was examined by immunofluorescence (FIG. 1B). At 48 h post-transduction, a high fraction of cells were immunostained with a pattern suggesting that sE$_{WNV}$ migrated through the secretory pathway.

The amount of physical particles in the vector stock used in this study was determined by a commercially available ELISA assay against the p24 HIV-1 capsid protein (Perkin Elmer Lifescience). The vector stock's actual titer was calculated on the basis of the transfer of vector DNA to target cells, using a quantitative PCR assay. The quantification of both a vector specific sequence (U5) and a cellular locus (CD3) gives the average vector DNA copy number per cell. This allows a precise titration of the vector preparation. The TRIP/sE$_{WNV}$ vector stock used in this study was titrated in human 293T cells at $5.2 \times 10^7$ transduction units (TU) per ml, (corresponding to approximately 900 TU/ng of p24 in human 293T cells). For simplicity reasons, we will express, in the following sections, the quantity of vector particles used as ng of p24 antigen.

Example 3

A Single Immunization with TRIP/sE$_{WNV}$ Induces Strong Antibody Responses

To assess the humoral immune response induced by the lentiviral vector expressing sE$_{WNV}$, groups of adult 129 mice were inoculated i.p with a single dose of vector particles equivalent to 500 ng of p24 antigen. Vectors coded either for sE$_{WNV}$ or for GFP protein as a control. Mice were bled periorbitally at 6, 13, 20 or 27 days post-immunization, and individual or pooled sera were tested for anti-WNV total antibodies, IgG and IgM using an already described isotype specific ELISA [29]. In vitro neutralizing activity of sera was assayed by a focus reduction neutralization test (FNRT) [29].

Figure 2:
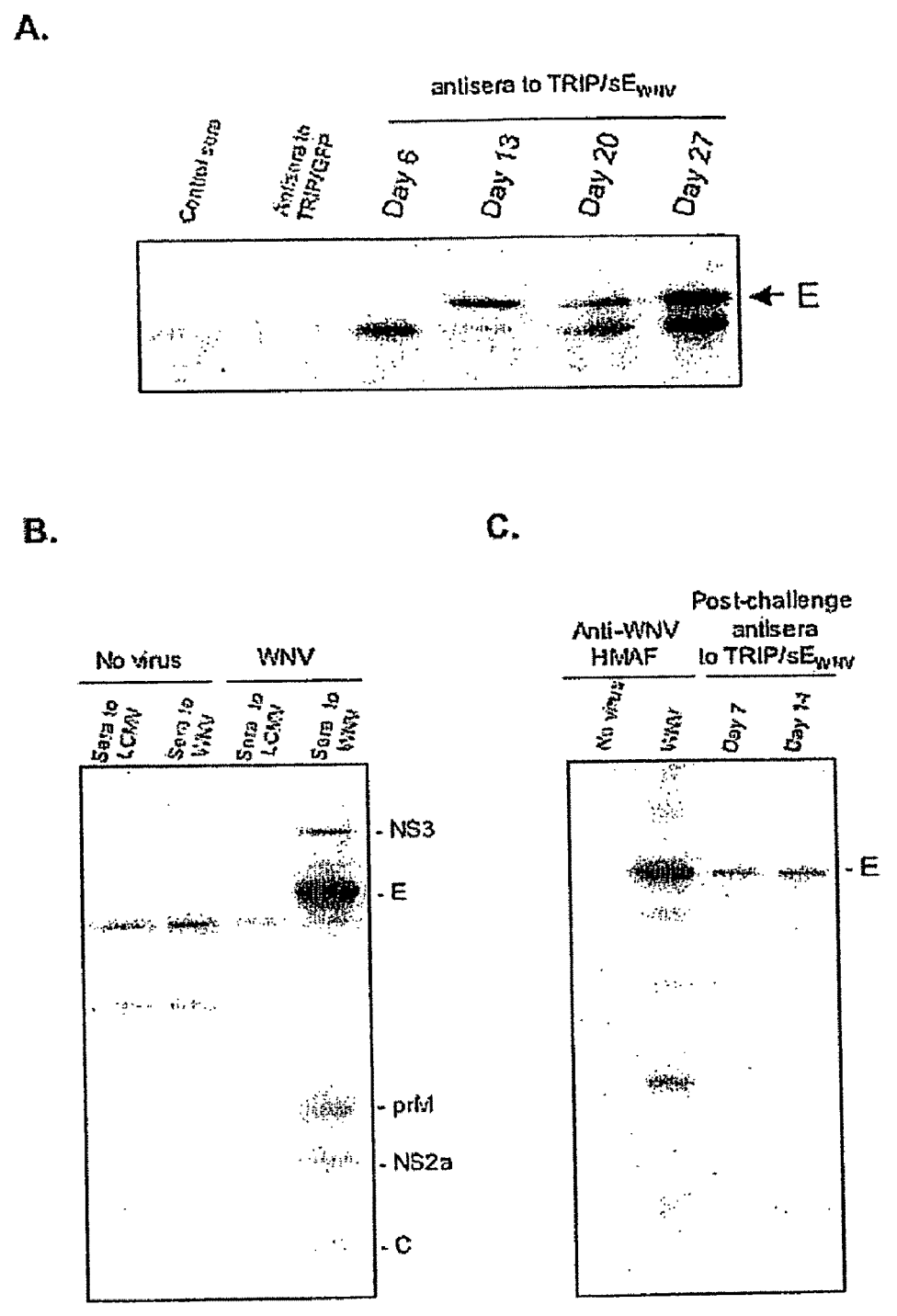

No anti-WNV antibodies were detected in sera of TRIP/GFP immunized control mice. Sera from TRIP/sE$_{WNV}$ immunized mice were first tested individually and very small differences between animals were observed (Mean±SD at day 6=0.5±0.3; day 13=1.3±0.05; day 21=1.3±0.15; day 27=1.4±0.15), thus in following experiments, pooled sera were used. In TRIP/sE$_{WNV}$ immunized mice, total antibodies against WNV were detectable as early as 6 days post immunization, although present at a low concentration. As expected at this time point, only anti-WNV IgM antibodies were detected in the immune sera. Total antibody responses increased 10-fold to reach a plateau at day 13, and were then maintained over time. At these later time points (day 13, 20, 27), IgM antibodies disappeared, to be replaced by IgG (Table 1). These sera were reactive with WNV E-glycoprotein from IS-98-ST1 infected Vero cell lysates as demonstrated by RIP assay (FIG. 2A).

A focus reduction neutralization test (FRNT) showed that sera from TRIP/sE$_{WNV}$ immunized mice contained detectable levels of neutralizing anti-WNV antibodies as early as 6 days post-immunization (Table 1). Together, these data show that an early and specific anti-WNV antibody immune response is mounted in mice inoculated with a single dose of TRIP/sE$_{WNV}$ vector particles.

TABLE 1

Antibody response of mice to inoculation with TRIP/sE$_{WNV}$

| Immunizing vector[a], | Day of bleeding | WNV antibody titer[b] | WNV IgM antibody titer[b] | WNV IgG antibody titer[b] | Anti-WNV FRNT$_{90}$[c] |
|---|---|---|---|---|---|
| TRIP/GFP | Day 27 | ND | ND | ND | <10 |
| TRIP/sE$_{WNV}$ | Day 06 | 3,000 | 300 | ND | 10 |
| | Day 13 | 30,000 | ND | 1,000 | 10 |
| | Day 20 | 30,000 | ND | 1,000 | 10 |
| | Day 27 | 30,000 | ND | 1,000 | 20 |

[a]Groups of 6 adult 129 mice were inoculated i.p. with a quantity of lentiviral vector particles corresponding to 500 ng of p24 antigen.

Example 4

Immunization with TRIP/sE$_{WNV}$ Confers Early Protection of Mice Against WNV Encephalitis In order to establish if the humoral immunity elicited in mice after TRIP/sE$_{WNV}$ vaccination was protective, advantage was taken of a mouse model for WNV challenge. Indeed, some mice strains are extremely sensitive to WNV challenge [31, 41], they develop a neuroinvasive lethal disease similar to that found in humans [32, 42] and die within few days post-inoculation. Groups of 129 mice that received a single dose of 500 ng p24 of TRIP/sE$_{WNV}$ or TRIP/GFP vector particles were i.p. challenged with 1,000 i.p. LD$_{50}$ of WNV strain IS-98-ST1 one or two weeks after priming.

Remarkably, all mice immunized with TRIP/sE$_{WNV}$ were protected against a high viral challenge (1,000 i.p. LD$_{50}$) as early as 7 days after priming. All mice immunized with the control vector TRIP/GFP or with DPBS died within 11 days of challenge (Table 2). Interestingly, total antibodies against WNV increased by ten-fold after challenge, suggesting that an effective secondary response was mounted in TRIP/sE$_{WNV}$ immunized mice (Table 2). Equivalent results were obtained in BALB/c mice (data not shown). These results indicate that TRIP/sE$_{WNV}$ vaccination confers a very quick, fully protective immune response

TABLE 2

Rapid protection by TRIP/sE$_{WNV}$ against WNV infection

| Immunizing vector[a], | day of challenge | Protection[b] (n° of surviving/n° of infected) | Post-challenge WNV antibody titer[c] |
|---|---|---|---|
| DPBS | Day 7 | 0/2 | NA |
| | Day 14 | 0/2 | NA |
| TRIP/GFP | Day 7 | 0/2 | NA |
| | Day 14 | 0/2 | NA |
| TRIP/sE$_{WNV}$ | Day 7 | 6/6 | 200,000 |
| | Day 14 | 6/6 | 300,000 |

[a] Groups of adult 129 mice were inoculated i.p. with a single dose of lentiviral vector particles corresponding to 500 ng of p24 antigen or with DPBS.

against a high WNV challenge.

Example 5

Immunization with TRIP/sE$_{WNV}$ Elicits Sterilizing Antiviral Immunity

To address whether or not WNV primo-infection can take place in vaccinated animals upon challenge, RIP assays were performed on pooled sera from immunized mice collected before and 21 days after WNV challenge.

The E protein was first detectable by RIP assay at day 13 post-immunization using pooled sera from TRIP/sE$_{WNV}$ immunized mice (FIG. 2A). The lack of detection of antibodies to E in one-week immune sera can be attributed to the low avidity of protein A for IgM in our RIP assay. Sera from TRIP/GFP control immunized mice did not react with WNV E protein.

Importantly, post-challenge sera from TRIP/sE$_{WNV}$ vaccinated mice did not precipitate any viral protein other than the E (FIG. 2C). This lack of reactivity against any WNV proteins other than E (such as preM and non structural proteins NS2a, NS2b and NS3) clearly indicates the absence of in vivo WNV replication upon challenge in vaccinated animals. In the BALB/c-MBT mice strain, which is resistant to the WNV encephalitis, sera are readily reactive to all viral proteins (Fi 2B). Thus, TRIP/sE$_{WNV}$ vaccination confers full sterilizing immunity to mice.

Example 6

Protection Provided by a Single Injection of Trip/sE$_{WNV}$ is Long Lasting We next determined whether a single immunization with the lentiviral vector-based vaccine has the potential to elicit long-term protective immunity against WNV infection. Groups of 129 mice were i.p. immunized with TRIP/sE$_{WNV}$ vector particles equivalent to 500 ng of p24 antigen or the same amount of TRIP/GFP vector as a control. Three months later, mice were bled periorbitally and pooled sera from each group were tested by ELISA and FRNT. Antibody levels in TRIP/sE$_{WNV}$ immunized mice were still remarkably high 3 months after a single vector injection (1:30,000), and neutralizing antibodies persisted (Table 3). Mice were then challenged i.p. with a 1,000 LD$_{50}$ dose of IS-98-ST1 WNV. Neither morbidity nor mortality were observed in mice immunized with TRIP/sE$_{WNV}$ whereas all control mice died within 10 days (Table 3). Total antibody titers as well as neutralizing anti-WNV antibodies increased after challenge, suggesting that an effective secondary response was mounted in mice immunized with a TRIP/sE$_{WNV}$ three months earlier (Table 3).

Thus, a single dose of the sE$_{WNV}$ coding lentiviral vector is efficient for providing long-term protective immunity in mice.

TABLE 3

Long-term protection by TRIP/sE$_{WNV}$ against WNV infection

| Immunizing vector[a] | WNV antibody titer[b] (pre-challenge) | Anti-WNV FRNT$_{90}$[c] (pre-challenge) | Protection[d] n° of surviving/ n° of infected | WNV antibody titer[b] (post-challenge) | Anti-WNV FRNT$_{90}$[c] (post-challenge) |
|---|---|---|---|---|---|
| TRIP/GFP | ND | <10 | 0/3 | NA | NA |
| TRIP/sE$_{WNV}$ | 30,000 | 20 | 13/13 | 500,000 | 400 |

[a]Groups of adult 129 mice were immunized i.p. with lentiviral vector particles corresponding to 500 ng of p24 antigen.
[b]Determined by ELISA on pooled heat-inactivated sera.
[c]FRNT: Focus Reduction Neutralization Test: the highest serum dilution that reduced the number of FFU of WNV by at least 90%.
[d]Mice were inoculated i.p. with 1,000 LD$_{50}$ of WNV strain IS-98-ST1, three months post immunization. Survival was recorded for 21 days.
ND: not detected (<100)
NA: not applicable

Example 7

A Single Minute Dose of TRIP/sE$_{WNV}$ Confers Full and Rapid Protection

In order to determine the minimum protective vaccine dose, groups of 129 mice were inoculated once with a wide range of TRIP/sE$_{WNV}$ vaccine doses varying from 1.5 ng to 500 ng of p24 antigen. One week after priming, immunized mice were challenged i.p. with 1,000 LD$_{50}$ IS-98-ST1 WNV. As expected, all mice that received 500 ng of p24 of the control TRIP/GFP vector died within 11-13 days after challenge. A 100% protection was achieved after injection of a single TRIP/sE$_{WNV}$ vector dose as low as 50 ng of p24. Lower doses conferred only partial protection thus allowing us to calculate a 50% protective dose in adult mice of 6.2 ng of p24 antigen (Table 4). Of note, these dose-protection experiments were performed in the most stringent challenge conditions, with an early challenge at day 7 post-vaccination and with a high lethal virus challenge inoculum (1,000 LD$_{50}$). Since total antibody concentrations increased by ten-fold between days 7 and 14 (Table 1), it is probable that the 50% protective dose would have been even lower than 6.2 ng if determined only one week later.

These results demonstrate that a minute dose of vector particles achieves quick and fully protective immunity in mice. This 100% protection is the consequence of an actual in vivo cell transduction by the vector particles. A heat treatment (10 min at 70° C.) of the vector particles that abrogates the transduction capability of lentiviral vectors (FIG. 3) also abrogates protection (Table 4), ruling out the possibility of a protection conferred by plasmid DNA or residual sE$_{WNV}$ proteins contaminating the vector stock.

TABLE 4

Dose-dependent protection by TRIP/sE$_{WNV}$ against WNV infection

| Immunizing vector[a], | dose (ng of p24) | Protection[b] n° of surviving/n° of infected | Post-challenge WNV antibody titer[c] |
|---|---|---|---|
| TRIP GFP | 500 | 0/6 | NA |
| Heat-inactivated TRIP/sE$_{WNV}$[d] | 50 | 0/6 | NA |
| TRIP/sE$_{WNV}$ | 500 | 6/6 | 200,000 |
|  | 150 | 6/6 | 300,000 |
|  | 50 | 12/12 | 300,000 |
|  | 15 | 5/6 | 300,000 |
|  | 5 | 2/5 | 200,000 |
|  | 1.5 | 1/12 | NA |

[a]Groups of adult 129 mice were inoculated i.p. with a single dose of lentiviral vector particles.
[b]Mice were inoculated i.p. with 1000 LD50 of WNV strain IS-98-ST1 one week after priming. Survival was recorded for 21 days.
[c]Determined by ELISA on pooled heat-inactivated sera.
[d]Lentiviral vector particles were heat-inactivated for 10 min at 70° C.
NA: Not Applicable This invention provides the first evidence that lentiviral vectors are efficient tools for eliciting a protective humoral immune response against a pathogen. In addition to the now well-described capacity of these vectors for inducing strong cellular immune responses [12-15, 17, 18, 21], this work broadens the applicability of lentiviral vectors as vaccination tools against pathogens for which a neutralizing humoral response is one active arm of the immune system.

The TRIP/sE$_{WNV}$ vector was able to induce a very early, long-lasting, fully protective immune response against WNV regardless of the lethal dose used in mice. Importantly, this immunity was achieved by a single immunization with a minute dose of vector particles.

These features make of TRIP/sE$_{WNV}$ a promising vaccine candidate against WNV. In particular, the urgent need for an efficient veterinary vaccine that could be used in susceptible animal populations in the event of a WNV outbreak, justifies trials involving the lentiviral TRIP/sE$_{WNV}$ vector in animals, notably horses and birds. Furthermore, the prophylactic immunization of large groups of animals with lentiviral vector-based vaccines would also serve as solid toxicity and safety proofs of concepts, providing the necessary hindsight and eventually paving the way for the possible use of lentiviral vectors as prophylactic vaccination tools in humans.

Several lines of arguments make the TRIP/sE$_{WNV}$ lentiviral vector a powerful candidate vaccine for veterinary use. Firstly, the provided protection takes place soon after immunization. This could be of major importance in the context of a WNV outbreak where rapid protection of sensitive animals is crucial. The exact nature of this early protective immune response has not been fully addressed. One week after immunization IgG antibodies are not yet detectable and IgM antibodies probably account for the observed protection. Passive transfer of polyclonal anti-WNV IgM has been shown to protect mice from WNV challenge, demonstrating the critical role of this isotype in controlling the early phases of WNV infection [43]. Nevertheless, we cannot exclude the contribution of innate or adaptive cellular responses against WNV antigens to the early protection observed [44]. Secondly, the TRIP/sE$_{WNV}$ lentiviral vector is fully effective with a single minute dose. This makes this candidate vaccine interestingly cost-effective, and could allow the development of protocols for mass vaccination, of particular interest for the protection of poultry. It is important to note that the dose required for full protective immunity could have even been overestimated in our mouse experimental protocol. Indeed, it has been shown that murine cells have a lower permissivity to lentiviral vector transduction than other mammal cells, including human cells (data not shown and [4, 45]). Avian cells show a better permissivity to transduction than murine cells (data not shown) allowing to predict that minute lentiviral vector vaccine doses would be effective in fowl. Furthermore, the 50% protective dose of 6.2 ng of p24 antigen of TRIP/sE$_{WNV}$ vector particles was calculated under the most stringent challenge conditions (early challenge at day 7 post-vaccination and a lethal dose of 1,000 LD$_{50}$). Given that total antibody concentrations increase by ten-fold between day 7 and 14, the 50% protective dose would probably have been even lower than 6.2 ng if calculated only one week later. Thirdly, by virtue of the ubiquitous tropism of the VSV-G envelope used for pseudotyping the vector particles [37], the lentiviral vector vaccine can theoretically be used, with no modification, in any vertebrate species: horses, fowl and zoo mammals at risk. A final consideration is that the protective immunity conferred by the vector is sterilizing, no viral replication takes place after WNV challenge. This could represent an important advantage if the vaccine were to be used for bird-immunization. Indeed, while horses, humans and other mammals are believed to be dead-end hosts of WNV infection, birds are known to be amplifying hosts and participate in the maintenance of an epidemic [30]. Moreover, recent literature shows that experimentally WNV infected hamsters that survive the acute illness can continue shedding infectious WNV in urine for up to 52 days [46]. If this can be generalized to other WNV susceptible mammals, a sterilizing vaccine could become crucial for the control of the WNV epidemic.

Several WNV vaccines for veterinary use have been proposed. One licensed in the US in 2003 for horses is an inactivated and adjuvanted virus (Fort Dodge website: www.e-quinewestnile.com). This inactivated preparation elicits low magnitude humoral responses in horses and thus requires several injections, followed by annual boosts. This killed virus vaccine does not elicit neutralizing antibodies in Chilean Flamingos and Red-tail hawks [47]. A recombinant canary pox encoding the preM/E proteins of the WNV has also been licensed in 2004 [48]. However this candidate also requires two injections at 5 weeks intervals. Neither vaccine provides absolute protection to the vaccinated horses. Other strategies, such as naked DNA encoding pre M and E proteins of WNV [28] are also envisioned.

Candidate vaccines against WNV are for the most part being developed for human use. A live measles vaccine expressing the secreted form of the E-glycoprotein of WNV has been shown to efficiently protect mice against WNV encephalitis [29]. Two recombinant live-attenuated vaccines, chimeric WNV/yellow fever and WNV/Dengue 4, containing the pre M and E genes of WNV cloned into the backbone of either the 17D vaccine strain of yellow fever virus or the dengue 4 virus, have been tested. Preclinical studies in mice and macaques show that both vaccines are protective against WNV challenge [49-51]. However, the use of chimeric live-attenuated virus might pose safety concerns: recombination between different flavivirus species is possible, as demonstrated by naturally occurring recombinants flaviviruses [52, 53].

The potential use of lentiviral vector-based vaccines, for human or veterinary use, will require careful design of the vector and rigorous pre-clinical safety studies. Safety concerns about the use of integrative vectors are justified in front of the recent reports of leukemia cases in the SCID. X1 trial.

These severe adverse effects are directly linked to the integration of the Moloney-derived retroviral vector at close proximity of the LMO2 proto-oncogene in hematopoietic stem cells [54].

However, vaccination applications of lentiviral vectors present lower risks. As opposed to stem cell-based gene therapy, which involves extensive proliferation of transduced cells and persistence of the genetic modification for the entire life of the patient, transduced cells in a vaccination scenario express the relevant antigen, and thus are targets of the elicited immune response. Cells expressing the antigen, whether APCs or not, are thought to be eliminated from the vaccinated organism within weeks or months. Furthermore, in the particular case of vaccination by sub-cutaneous or intravenous injections, it has been shown that VSV-G pseudotyped lentiviral vector particles target essentially DCs [13, 18], a non dividing professional APC with short in vivo half life upon activation. Nevertheless, both vector cell tropism and lack of persistence of vaccination vector sequences, depending on the route of injection and vector dose, will have to be carefully addressed for each vaccination protocol.

Lentiviral vectors appear to be promising tools for vaccination against West Nile Virus and likely other zoonoses or emerging pathogens.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

1. Sirven A, Pflumio F, Zennou V, et al. The human immunodeficiency virus type-1 central DNA flap is a crucial determinant for lentiviral vector nuclear import and gene transduction of human hematopoietic stem cells. *Blood* 2000; 96:4103-4110.
2. Zennou V, Serguera C, Sarkis C, et al. The HIV-1 DNA flap stimulates HIV vector-mediated cell transduction in the brain. *Nat Biotechnol* 2001; 19:446-450.
3. Takahashi M, Miyoshi H, Verma I M, et al. Rescue from photoreceptor degeneration in the rd mouse by human immunodeficiency virus vector-mediated gene transfer. *J Virol* 1999; 73:7812-7816.
4. Giannini C, Morosan S, Tralhao J G, et al. A highly efficient, stable, and rapid approach for ex vivo human liver gene therapy via a FLAP lentiviral vector. *Hepatology* 2003; 38:114-122.
5. Kootstra N A, Matsumura R, and Verma I M. Efficient production of human FVIII in hemophilic mice using lentiviral vectors. *Mol Ther* 2003; 7:623-631.
6. Kordower J H, Emborg M E, Bloch J, et al. Neurodegeneration prevented by lentiviral vector delivery of GDNF in primate models of Parkinson's disease. *Science* 2000; 290:767-773.
7. Benhamida S, Pflumio F, Dubart-Kupperschmitt A, et al. Transduced CD34+ cells from adrenoleukodystrophy patients with HIV-derived vector mediate long-term engraftment of NOD/SCID mice. *Mol Ther* 2003; 7:317-324.
8. Biffi A, De Palma M, Quattrini A, et al. Correction of metachromatic leukodystrophy in the mouse model by transplantation of genetically modified hematopoietic stem cells. *J Clin Invest* 2004; 113:1118-1129.
9. Pawliuk R, Westerman K A, Fabry M E, et al. Correction of sickle cell disease in transgenic mouse models by gene therapy. *Science* 2001; 294:2368-2371.
10. Puthenveetil G, Scholes J, Carbonell D, et al Successful correction of the human beta-thalassemia major phenotype using a lentiviral vector. *Blood* 2004; 104:3445-3453.
11. Ralph G S, Radcliffe P A, Day D M, et al Silencing mutant SOD1 using RNAi protects against neurodegeneration and extends survival in an ALS model. *Nat Med* 2005; 11:429-433.
12. Breckpot K, Dullaers M, Bonehill A, et al Lentivirally transduced dendritic cells as a tool for cancer immunotherapy. *J Gene Med* 2003; 5:654-667.
13. Esslinger C, Chapatte L, Finke D, et al. In vivo administration of a lentiviral vaccine targets DCs and induces efficient CD8(+) T cell responses. *J Clin Invest* 2003; 111:1673-1681.
14. Esslinger C, Romero P, and MacDonald H R. Efficient transduction of dendritic cells and induction of a T-cell response by third-generation lentivectors. *Hum Gene Ther* 2002; 13:1091-1100.
15. Firat H, Zennou V, Garcia-Pons F, et al. Use of a lentiviral flap vector for induction of CTL immunity against melanoma. Perspectives for immunotherapy. *J Gene Med* 2002; 4:3845.
16. He Y, Zhang J, Mi Z, et al Immunization with lentiviral vector-transduced dendritic cells induces strong and long-lasting T cell responses and therapeutic immunity. *J Immunol* 2005; 174:3808-3817.
17. Metharom P, Ellem K A, Schmidt C, et al. Lentiviral vector-mediated tyrosinase-related protein 2 gene transfer to dendritic cells for the therapy of melanoma. *Hum Gene Ther* 2001; 12:2203-2213.
18. Palmowski M J, Lopes L, Ikeda Y, et al. Intravenous injection of a lentiviral vector encoding NY-ESO-1 induces an effective CTL response. *J Immunol* 2004; 172:1582-1587.
19. Dyall J, Latouche J B, Schnell S, et al. Lentivirus-transduced human monocyte-derived dendritic cells efficiently stimulate antigen-specific cytotoxic T lymphocytes. *Blood* 2001; 97:114-121.
20. Rohrlich P S, Cardinaud S, Lule J, et al. Use of a lentiviral vector encoding a HCMV-chimeric IE1-pp65 protein for epitope identification in HLA-Transgenic mice and for ex vivo stimulation and expansion of CD8(+) cytotoxic T cells from human peripheral blood cells. *Hum Immunol* 2004; 65:514-522.
21. Zarei S, Abraham S, Arrighi J F, et al. Lentiviral transduction of dendritic cells confers protective antiviral immunity in vivo. *J Virol* 2004; 78:7843-7845.
22. VandenDriessche T, Thorrez L, Naldini L, et al. Lentiviral vectors containing the human immunodeficiency virus type-1 central polypurine tract can efficiently transduce nondividing hepatocytes and antigen-presenting cells in vivo. *Blood* 2002; 100:813-822.
23. Engle M J, and Diamond M S. Antibody prophylaxis and therapy against West Nile virus infection in wild-type and immunodeficient mice. *J Virol* 2003; 77:12941-12949.
24. Diamond M S, Shrestha B, Marri A, et al. B cells and antibody play critical roles in the immediate defense of disseminated infection by West Nile encephalitis virus. *J Virol* 2003; 77:2578-2586.
25. Ben-Nathan D, Lustig S, Tam G, et al. Prophylactic and therapeutic efficacy of human intravenous immunoglobulin in treating West Nile virus infection in mice. *J Infect Dis* 2003; 188:5-12.

26. Beasley D W, and Barrett A D. Identification of neutralizing epitopes within structural domain III of the West Nile virus envelope protein. *J Virol* 2002; 76: 13097-13100.
27. Wang T, Anderson J F, Magnarelli L A, et al. Immunization of mice against West Nile virus with recombinant envelope protein. *J Immunol* 2001; 167:5273-5277.
28. Davis B S, Chang G J, Cropp B, et al. West Nile virus recombinant DNA vaccine protects mouse and horse from virus challenge and expresses in vitro a noninfectious recombinant antigen that can be used in enzyme-linked immunosorbent assays. *J Virol* 2001; 75:4040-4047.
29. Despres P, Combredet C, Frenkiel M P, et al. Live measles vaccine expressing the secreted form of the West Nile virus envelope glycoprotein protects against West Nile virus encephalitis. *J Infect Dis* 2005; 191:207-214.
30. Dauphin G, Zientara S, Zeller H, et al. West Nile: worldwide current situation in animals and humans. *Comp Immunol Microbiol Infect Dis* 2004; 27:343-355.
31. Mashimo T, Lucas M, Simon-Chazottes D, et al. A nonsense mutation in the gene encoding 2'-5'-oligoadenylate synthetase/L1 isoform is associated with West Nile virus susceptibility in laboratory mice. *Proc Natl Acad Sci USA* 2002; 99:11311-11316.
32. Lucas M, Frenkiel M P, Mashimo T, et al. The Israeli strain IS-98-ST1 of West Nile virus as viral model for West Nile encephalitis in the Old World. *Virol J* 2004; 1:9.
33. Lanciotti R S, Ebel G D, Deubel V, et al. Complete genome sequences and phylogenetic analysis of West Nile virus strains isolated from the United States, Europe, and the Middle East. *Virology* 2002; 298:96-105.
34. Charrel R N, Brault A C, Gallian P, et al. Evolutionary relationship between Old World West Nile virus strains. Evidence for viral gene flow between Africa, the Middle East, and Europe. *Virology* 2003; 315:381-388.
35. Despres P, Frenkiel M P, and Deubel V. Differences between cell membrane fusion activities of two dengue type-1 isolates reflect modifications of viral structure. *Virology* 1993; 196:209-219.
36. Zufferey R, Nagy D, Mandel R J, et al. Multiply attenuated lentiviral vector achieves efficient gene delivery in vivo. *Nat Biotechnol* 1997; 15:871-875.
37. Yee J K, Miyanohara A, LaPorte P, et al. A general method for the generation of high-titer, pantropic retroviral vectors: highly efficient infection of primary hepatocytes. *Proc Natl Acad Sci USA* 1994; 91:9564-9568.
38. Zennou V, Petit C, Guetard D, et al. HIV-1 genome nuclear import is mediated by a central DNA flap. *Cell* 2000; 101:173-185.
39. Brussel A, and Sonigo P. Analysis of early human immunodeficiency virus type 1 DNA synthesis by use of a new sensitive assay for quantifying integrated provirus. *J Virol* 2003; 77: 10119-10124.
40. Despres P, Griffin J W, and Griffin D E. Effects of anti-E2 monoclonal antibody on sindbis virus replication in AT3 cells expressing bcl-2. *J Virol* 1995; 69:7006-7014.
41. Deubel V, Fiette L, Gounon P, et al. Variations in biological features of West Nile viruses. *Ann NY Acad Sci* 2001; 951:195-206.
42. Ceccaldi P E, Lucas M, and Despres P. New insights on the neuropathology of West Nile virus. *FEMS Microbiol Lett* 2004; 233:1-6.
43. Diamond M S, Sitati E M, Friend L D, et al. A critical role for induced IgM in the protection against West Nile virus infection. *J Exp Med* 2003; 198:1853-1862.
44. Shrestha B, and Diamond M S. Role of CD8+ T cells in control of West Nile virus infection. *J Virol* 2004; 78:8312-8321.
45. Nguyen T H, Oberholzer J, Birraux J, et al. Highly efficient lentiviral vector-mediated transduction of nondividing, fully reimplantable primary hepatocytes. *Mol Ther* 2002; 6: 199-209.
46. Tonry J H, Xiao S Y, Siirin M, et al. Persistent shedding of West Nile virus in urine of experimentally infected hamsters. *Am J Trop Med Hyg* 2005; 72:320-324.
47. Nusbaum K E, Wright J C, Johnston W B, et al. Absence of humoral response in flamingos and red-tailed hawks to experimental vaccination with a killed West Nile virus vaccine. *Avian Dis* 2003; 47:750-752.
48. Minke J M, Siger L, Karaca K, et al. Recombinant canarypoxvirus vaccine carrying the prM/E genes of West Nile virus protects horses against a West Nile virus-mosquito challenge. *Arch Virol Suppl* 2004:221-230.
49. Arroyo J, Miller C, Catalan J, et al. ChimeriVax-West Nile virus live-attenuated vaccine: preclinical evaluation of safety, immunogenicity, and efficacy. *J Virol* 2004; 78:12497-12507.
50. Pletnev A G, Putnak R, Speicher J, et al. West Nile virus/dengue type 4 virus chimeras that are reduced in neurovirulence and peripheral virulence without loss of immunogenicity or protective efficacy. *Proc Natl Acad Sci USA* 2002; 99:3036-3041.
51. Pletnev A G, Claire M S, Elkins R, et al. Molecularly engineered live-attenuated chimeric West Nile/dengue virus vaccines protect rhesus monkeys from West Nile virus. *Virology* 2003; 314:190-195.
52. Seligman S J, and Gould E A. Live flavivirus vaccines: reasons for caution. *Lancet* 2004; 363:2073-2075.
53. Gould E A, Moss S R, and Turner S L. Evolution and dispersal of encephalitic flaviviruses. *Arch Virol Suppl* 2004:65-84.
54. Hacein-Bey-Abina S, Von Kalle C, Schmidt M, et al. LMO2-associated clonal T cell proliferation in two patients after gene therapy for SCID-XL. *Science* 2003; 302:415-419.

What is claimed is:

1. A method for generating an immune response against a West Nile virus antigen comprising administering to an animal a single dose of 5-500 ng of lentiviral p24 antigen of a lentiviral vector encoding the West Nile virus antigen;
   wherein the lentiviral vector comprises a lentiviral central polypurine tract and cis-acting region for termination; and
   wherein the administration of the single dose of the lentiviral vector induces a detectable IgG response against the encoded West Nile virus antigen at 13 days after the administration.

2. The method of claim 1, wherein the method comprises administering a single dose of 5-15 ng of lentiviral p24 antigen.

3. The method of claim 1, wherein the method comprises administering a single dose of 15-50 ng of lentiviral p24 antigen.

4. The method of claim 1, wherein the method comprises administering a single dose of 50-150 ng of lentiviral p24 antigen.

5. The method of claim 1, wherein the method comprises administering a single dose of 150-500 ng of lentiviral p24 antigen.

6. The method of claim 1, wherein the West Nile virus antigen is an envelope glycoprotein antigen.

7. The method of claim 6, wherein the lentiviral vector encodes a truncated West Nile virus E protein.

8. The method of claim 7, wherein the lentiviral vector encodes a secreted, truncated West Nile virus E protein, from which the membrane anchoring region has been removed.

9. The method of claim 8, wherein the lentiviral vector encodes a secreted, truncated West Nile virus E protein comprising amino acid residues 1-441 of the West Nile virus strain IS-98-ST1 E protein.

10. The method of claim 7, wherein the lentiviral vector encodes a signal peptide of a West Nile virus M protein precursor protein.

11. The method of claim 8, wherein the lentiviral vector encodes a signal peptide of a West Nile virus M protein precursor protein.

12. The method of claim 9, wherein the lentiviral vector encodes a signal peptide of a West Nile virus M protein precursor protein.

13. The method of claim 1, wherein the lentiviral vector is administered by an intraperitoneal, intravenous, or intramuscular route.

14. The method of claim 1, wherein the animal is a human.

15. The method of claim 8, wherein the method comprises administering a single dose of 5-15 ng of lentiviral p24 antigen.

16. The method of claim 8, wherein the method comprises administering a single dose of 15-50 ng of lentiviral p24 antigen.

17. The method of claim 8, wherein the method comprises administering a single dose of 50-150 ng of lentiviral p24 antigen.

18. The method of claim 8, wherein the method comprises administering a single dose of 150-500 ng of lentiviral p24 antigen.

19. The method of claim 11, wherein the method comprises administering a single dose of 5-15 ng of lentiviral p24 antigen.

20. The method of claim 11, wherein the method comprises administering a single dose of 15-50 ng of lentiviral p24 antigen.

21. The method of claim 11, wherein the method comprises administering a single dose of 50-150 ng of lentiviral p24 antigen.

22. The method of claim 11, wherein the method comprises administering a single dose of 150-500 ng of lentiviral p24 antigen.

* * * * *

SEQUENCE LISTING

```
<160> NUMBER OF SEQ ID NOS: 13

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
```

-continued

```
cacaacagac gggcacacac tacttga                                         27

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
cactcaaggc aagctttatt gaggc                                           25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gctagagatt ttccacactg actaa                                           25

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggctaactag ggaacccact g                                               21

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
ggctgaaggt tagggatacc aatattcctg tctc                                 34

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
ctagtgatgg gctcttccct tgagcccttc                                      30

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggctatcatt cttcttcaag gta                                             23
```

```
<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cctctcttca gccatttaag ta                                              22

<210> SEQ ID NO 9
<211> LENGTH: 1380
<212> TYPE: DNA
<213> ORGANISM: West Nile virus

<400> SEQUENCE: 9
atgagagttg tgtttgtcgt gctattgctt ttggtggccc cagcttacag cttcaactgc     60
cttggaatga gcaacagaga cttcttggaa ggagtgtctg gagcaacatg ggtggatttg    120
gttctcgaag gcgacagctg cgtgactatc atgtctaagg acaagcctac catcgatgtg    180
aagatgatga atatggaggc ggtcaacctg gcagaggtcc gcagttattg ctatttggct    240
accgtcagcg atctctccac caaagctgcg tgcccgacca tgggagaagc tcacaatgac    300
aaacgtgctg acccagcttt tgtgtgcaga caaggagtgg tggacagggg ctggggcaac    360
ggctgcggat tatttggcaa aggaagcatt gacacatgcg ccaaatttgc ctgctctacc    420
aaggcaatag gaagaaccat cttgaaagag aatatcaagt acgaagtggc cattttttgtc    480 catgaccaa ctactgtgga gtcgcacgga aactactcca cacaggttgg agccactcag    540
gcagggagat tcagcatcac tcctgcggcg ccttcataca cactaaagct tggagaatat    600
ggagaggtga cagtgactg tgaaccacgg tcagggattg acaccaatgc atactacgtg    660
atgactgttg aacaaagac gttcttggtc catcgtgagt ggttcatgga cctcaacctc    720
ccttggagca gtgctggaag tactgtgtgg aggaacagag agacgttaat ggagtttgag    780
gaaccacacg ccacgaagca gtctgtgata gcattgggct cacaagaggg agctctgcat    840 caagcttttgg ctggagccat tcctgtggaa ttttcaagca cactgtcaa gttgacgtcg    900 ggtcatttga agtgtagagt gaagatggaa aaattgcagt tgaagggaac aacctatggc    960
gtctgttcaa aggctttcaa gtttcttggg actcccgcag acacaggtca cggcactgtg   1020
gtgttggaat tgcagtacac tggcacggat ggaccttgca aagttcctat ctcgtcagtg   1080
gcttcattga acgacctaac gccagtgggc agattggtca ctgtcaaccc ttttgtttca   1140
gtggccacgg ccaacgctaa ggtcctgatt gaattggaac acccctttgg agactcatac   1200
atagtggtgg gcagaggaga acaacagatc aatcaccatt ggcacaagtc tggaagcagc   1260
attggcaaag cctttacaac caccctcaaa ggagcgcaga ctagccgc tctaggagac     1320 acagcttggg actttggatc agttggaggg gtgttcacct cagttgggaa ggctgtctaa   1380

<210> SEQ ID NO 10
<211> LENGTH: 1374
<212> TYPE: DNA
<213> ORGANISM: West Nile virus

<400> SEQUENCE: 10
agagttgtgt tgtcgtgct attgcttttg gtggccccag cttacagctt caactgcctt     60
ggaatgagca acagagactt cttggaagga gtgtctggag caacatgggt ggatttggtt   120
```

-continued

```
ctcgaaggcg acagctgcgt gactatcatg tctaaggaca agcctaccat cgatgtgaag      180
atgatgaata tggaggcggt caacctggca gaggtccgca gttattgcta tttggctacc      240
gtcagcgatc tctccaccaa agctgcgtgc ccgaccatgg gagaagctca caatgacaaa      300
cgtgctgacc cagcttttgt gtgcagacaa ggagtggtgg acaggggctg gggcaacggc      360 tgccggattat ttggcaaagg aagcattgac acatgcgcca aatttgcctg ctctaccaag      420
gcaataggaa gaaccatctt gaaagagaat atcaagtacg aagtggccat ttttgtccat      480
ggaccaacta ctgtggagtc gcacggaaac tactccacac aggttggagc cactcaggca      540
gggagattca gcatcactcc tgcggcgcct tcatacacac taaagcttgg agaatatgga      600
gaggtgacag tggactgtga accacggtca gggattgaca ccaatgcata ctacgtgatg      660
actgttggaa caaagacgtt cttggtccat cgtgagtggt tcatggacct caacctccct      720
tggagcagtg ctggaagtac tgtgtggagg aacagagaga cgttaatgga gtttgaggaa      780
ccacacgcca cgaagcagtc tgtgatagca ttgggctcac aagagggagc tctgcatcaa      840
gctttggctg agccattcc tgtggaattt tcaagcaaca ctgtcaagtt gacgtcgggt      900
catttgaagt gtagagtgaa gatggaaaaa ttgcagttga agggaacaac ctatggcgtc      960
tgttcaaagg ctttcaagtt tcttgggact cccgcagaca caggtcacgg cactgtggtg     1020
ttggaattgc agtacactgg cacggatgga ccttgcaaag ttcctatctc gtcagtggct     1080
tcattgaacg acctaacgcc agtgggcaga ttggtcactg tcaaccctttt gtttcagtg     1140 gccacggcca acgctaaggt cctgattgaa ttggaaccac cctttggaga ctcatacata     1200
gtggtgggca gaggagaaca acagatcaat caccattggc acaagtctgg aagcagcatt     1260
ggcaaagcct ttacaaccac cctcaaagga gcgcagagac tagccgctct aggagacaca     1320
gcttgggact ttggatcagt tggagggtg ttcacctcag ttgggaaggc tgtc            1374
```

<210> SEQ ID NO 11
<211> LENGTH: 458
<212> TYPE: PRT
<213> ORGANISM: West Nile virus

<400> SEQUENCE: 11

```
Arg Val Val Phe Val Val Leu Leu Leu Val Ala Pro Ala Tyr Ser
  1               5                  10                  15

Phe Asn Cys Leu Gly Met Ser Asn Arg Asp Phe Leu Glu Gly Val Ser
                 20                  25                  30

Gly Ala Thr Trp Val Asp Leu Val Leu Glu Gly Asp Ser Cys Val Thr
             35                  40                  45

Ile Met Ser Lys Asp Lys Pro Thr Ile Asp Val Lys Met Met Asn Met
         50                  55                  60

Glu Ala Val Asn Leu Ala Glu Val Arg Ser Tyr Cys Tyr Leu Ala Thr
     65                  70                  75                  80

Val Ser Asp Leu Ser Thr Lys Ala Ala Cys Pro Thr Met Gly Glu Ala
                 85                  90                  95

His Asn Asp Lys Arg Ala Asp Pro Ala Phe Val Cys Arg Gln Gly Val
            100                 105                 110

Val Asp Arg Gly Trp Gly Asn Gly Cys Gly Leu Phe Gly Lys Gly Ser
        115                 120                 125

Ile Asp Thr Cys Ala Lys Phe Ala Cys Ser Thr Lys Ala Ile Gly Arg
    130                 135                 140

Thr Ile Leu Lys Glu Asn Ile Lys Tyr Glu Val Ala Ile Phe Val His
145                 150                 155                 160
```

Gly Pro Thr Thr Val Glu Ser His Gly Asn Tyr Ser Thr Gln Val Gly
            165                 170                 175

Ala Thr Gln Ala Gly Arg Phe Ser Ile Thr Pro Ala Ala Pro Ser Tyr
            180                 185                 190

Thr Leu Lys Leu Gly Glu Tyr Gly Glu Val Thr Val Asp Cys Glu Pro
            195                 200                 205

Arg Ser Gly Ile Asp Thr Asn Ala Tyr Tyr Val Met Thr Val Gly Thr
210                 215                 220

Lys Thr Phe Leu Val His Arg Glu Trp Phe Met Asp Leu Asn Leu Pro
225                 230                 235                 240

Trp Ser Ser Ala Gly Ser Thr Val Trp Arg Asn Arg Glu Thr Leu Met
            245                 250                 255

Glu Phe Glu Glu Pro His Ala Thr Lys Gln Ser Val Ile Ala Leu Gly
            260                 265                 270

Ser Gln Glu Gly Ala Leu His Gln Ala Leu Ala Gly Ala Ile Pro Val
            275                 280                 285

Glu Phe Ser Ser Asn Thr Val Lys Leu Thr Ser Gly His Leu Lys Cys
            290                 295                 300

Arg Val Lys Met Glu Lys Leu Gln Leu Lys Gly Thr Thr Tyr Gly Val
305                 310                 315                 320

Cys Ser Lys Ala Phe Lys Phe Leu Gly Thr Pro Ala Asp Thr Gly His
            325                 330                 335

Gly Thr Val Val Leu Glu Leu Gln Tyr Thr Gly Thr Asp Gly Pro Cys
            340                 345                 350

Lys Val Pro Ile Ser Ser Val Ala Ser Leu Asn Asp Leu Thr Pro Val
            355                 360                 365

Gly Arg Leu Val Thr Val Asn Pro Phe Val Ser Val Ala Thr Ala Asn
370                 375                 380

Ala Lys Val Leu Ile Glu Leu Glu Pro Pro Phe Gly Asp Ser Tyr Ile
385                 390                 395                 400

Val Val Gly Arg Gly Glu Gln Gln Ile Asn His His Trp His Lys Ser
            405                 410                 415

Gly Ser Ser Ile Gly Lys Ala Phe Thr Thr Thr Leu Lys Gly Ala Gln
            420                 425                 430

Arg Leu Ala Ala Leu Gly Asp Thr Ala Trp Asp Phe Gly Ser Val Gly
            435                 440                 445

Gly Val Phe Thr Ser Val Gly Lys Ala Val
            450                 455

<210> SEQ ID NO 12
<211> LENGTH: 94
<212> TYPE: PRT
<213> ORGANISM: West Nile virus

<400> SEQUENCE: 12

Thr Thr Tyr Gly Val Cys Ser Lys Ala Phe Lys Phe Leu Gly Thr Pro
1               5                   10                  15

Ala Asp Thr Gly His Gly Thr Val Val Leu Glu Leu Gln Tyr Thr Gly
            20                  25                  30

Thr Asp Gly Pro Cys Lys Val Pro Ile Ser Ser Val Ala Ser Leu Asn
        35                  40                  45

Asp Leu Thr Pro Val Gly Arg Leu Val Thr Val Asn Pro Phe Val Ser
    50                  55                  60

Val Ala Thr Ala Asn Ala Lys Val Leu Ile Glu Leu Glu Pro Pro Phe
65                  70                  75                  80

Gly Asp Ser Tyr Ile Val Val Gly Arg Gly Glu Gln Gln Ile
                85                  90

<210> SEQ ID NO 13
<211> LENGTH: 4555
<212> TYPE: DNA
<213> ORGANISM: Artificial Sequence
<220> FEATURE:
<223> OTHER INFORMATION: Description of Artificial Sequence: Synthetic
      lentiviral vector pTRIP/Ewnv sequence

<400> SEQUENCE: 13

| | | | | | |
|---|---|---|---|---|---|
| tggaagggct | aattcactcc | caacgaagac | aagatatcct | tgatctgtgg | atctaccaca | 60 |
| cacaaggcta | cttccctgat | tagcagaact | acacaccagg | gccagggatc | agatatccac | 120 |
| tgacctttgg | atggtgctac | aagctagtac | cagttgagcc | agagaagtta | gaagaagcca | 180 |
| acaaaggaga | gaacaccagc | ttgttacaac | ctgtgagcct | gcatgggatg | gatgacccgg | 240 |
| agagagaagt | gttagagtgg | aggtttgaca | gccgcctagc | atttcatcac | ggtgcccga | 300 |
| gagctgcatc | cggagtactt | caagaactgc | tgatatcgag | cttgctacaa | gggactttcc | 360 |
| gctggggac | tttccaggga | ggcgtggcct | gggcgggact | ggggagtggc | gagccctcag | 420 |
| atcctgcata | taagcagctg | ctttttgcct | gtactgggtc | tctctggtta | gaccagatct | 480 |
| gagcctggga | gctctctggc | taactaggga | acccactgct | taagcctcaa | taaagcttgc | 540 |
| cttgagtgct | tcaagtagtg | tgtgcccgtc | tgttgtgtga | ctctggtaac | tagagatccc | 600 |
| tcagacccctt | ttagtcagtg | tggaaaatct | ctagcagtgg | cgcccgaaca | gggacttgaa | 660 |
| agcgaaaggg | aaaccagagg | agctctctcg | acgcaggact | cggcttgctg | aagcgcggaa | 720 |
| ttccgcgcca | cggcaagagg | cgaggggcgg | cgactggtga | gtacgccaaa | aattttgact | 780 |
| agcggaggct | agaaggagag | agatgggtgc | gagagcgtca | gtattaagcg | ggggagaatt | 840 |
| agatcgcgat | gggaaaaaat | tcggttaagg | ccagggggga | agaaaaaata | taaattaaaa | 900 |
| catatagtat | gggcaagcag | ggagctagaa | cgattcgcag | ttaatcctgg | cctgttagaa | 960 |
| acatcagaag | gctgtagaca | atactgggga | cagctacaac | catcccttca | gacaggatca | 1020 |
| gaagaactta | gatcattata | taatacagta | gcaaccctct | attgtgtgca | tcaaaggata | 1080 |
| gagataaaag | acaccaagga | agctttagac | aagatagagg | aagagcaaaa | caaaagtaag | 1140 |
| accaccgcac | agcaagcggc | cgctgatctt | cagacctgga | ggaggagata | tgagggacaa | 1200 |
| ttggagaagt | gaattatata | aatataaagt | agtaaaaatt | gaaccattag | gagtagcacc | 1260 |
| caccaaggca | aagagaagag | tggtgcagag | agaaaaaaga | gcagtgggaa | taggagcttt | 1320 |
| gttccttggg | ttcttgggag | cagcaggaag | cactatgggc | gcagcgtcaa | tgacgctgac | 1380 |
| ggtacaggcc | agacaattat | tgtctggtat | agtgcagcag | cagaacaatt | tgctgagggc | 1440 |
| tattgaggcg | caacagcatc | tgttgcaact | cacagtctgg | ggcatcaagc | agctccaggc | 1500 |
| aagaatcctg | gctgtggaaa | gatacctaaa | ggatcaacag | ctcctgggga | tttgggttg | 1560 |
| ctctggaaaa | ctcatttgca | ccactgctgt | gccttggaat | gctagttgga | gtaataaatc | 1620 |
| tctggaacag | atttggaatc | acacgacctg | gatggagtgg | gacagagaaa | ttaacaatta | 1680 |
| cacaagctta | atacactcct | taattgaaga | atcgcaaaac | cagcaagaaa | agaatgaaca | 1740 |
| agaattattg | gaattagata | aatgggcaag | tttgtggaat | tggtttaaca | taacaaattg | 1800 |
| gctgtggtat | ataaaattat | tcataatgat | agtaggaggc | ttggtaggtt | taagaatagt | 1860 |
| ttttgctgta | ctttctatag | tgaatagagt | taggcaggga | tattcaccat | tatcgtttca | 1920 |
| gacccacctc | ccaaccccga | ggggacccga | caggcccgaa | ggaatagaag | aagaaggtgg | 1980 |

```
agagagagac agagacagat ccattcgatt agtgaacgga tctcgacggt atcgccgaat    2040
tcacaaatgg cagtattcat ccacaattt aaaagaaaag gggggattgg ggggtacagt    2100 gcagggaaa gaatagtaga cataatagca acagacatac aaactaaaga attacaaaaa    2160
caaattacaa aaattcaaaa ttttcgggtt tattacaggg acagcagaga tccactttgg    2220
ggcgataagc ttgggagttc cgcgttacat aacttacggt aaatggcccg cctggctgac    2280
cgcccaacga ccccgccca ttgacgtcaa taatgacgta tgttcccata gtaacgccaa    2340
tagggacttt ccattgacgt caatgggtgg agtatttacg gtaaactgcc cacttggcag    2400
tacatcaagt gtatcatatg ccaagtacgc cccctattga cgtcaatgac ggtaaatggc    2460
ccgcctggca ttatgcccag tacatgacct tatgggactt tcctacttgg cagtacatct    2520
acgtattagt catcgctatt accatggtga tgcggttttg gcagtacatc aatgggcgtg    2580
gatagcggtt tgactcacgg ggatttccaa gtctccaccc cattgacgtc aatgggagtt    2640
tgttttggca ccaaaatcaa cgggactttc caaaatgtcg taacaactcc gccccattga    2700
cgcaaatggg cggtaggcgt gtacggtggg aggtctatat aagcagagct cgtttagtga    2760
accgtcagat cgcctggaga cgccatccac gctgttttga cctccataga agacaccgac    2820
tctagaggac gtacgatgag agttgtgttt gtcgtgctat tgcttttggt ggccccagct    2880
tacagcttca actgccttgg aatgagcaac agagacttct tggaaggagt gtctggagca    2940
acatgggtgg atttggttct cgaaggcgac agctgcgtga ctatcatgtc taaggacaag    3000
cctaccatcg atgtgaagat gatgaatatg gaggcggtca acctggcaga ggtccgcagt    3060
tattgctatt tggctaccgt cagcgatctc tccaccaaag ctgcgtgccc gaccatggga    3120
gaagctcaca atgacaaacg tgctgaccca gcttttgtgt gcagacaagg agtggtggac    3180
aggggctggg gcaacggctg cggattattt ggcaaaggaa gcattgacac atgcgccaaa    3240
tttgcctgct ctaccaaggc aataggaaga accatcttga aagagaatat caagtacgaa    3300
gtggccattt ttgtccatgg accaactact gtggagtcgc acggaaacta ctccacacag    3360
gttggagcca ctcaggcagg agattcagc atcactcctg cggcgccttc atacacacta    3420
aagcttggag aatatggaga ggtgacagtg gactgtgaac cacggtcagg gattgacacc    3480
aatgcatact acgtgatgac tgttggaaca aagacgttct tggtccatcg tgagtggttc    3540
atggacctca acctcccttg gagcagtgct ggaagtactg tgtggaggaa cagagagacg    3600
ttaatggagt tgaggaacc acacgccacg aagcagtctg tgatagcatt gggctcacaa    3660
gagggagctc tgcatcaagc tttggctgga gccattcctg tggaattttc aagcaacact    3720
gtcaagttga cgtcgggtca tttgaagtgt agagtgaaga tggaaaaatt gcagttgaag    3780
ggaacaacct atgcgtctg ttcaaaggct ttcaagtttc ttgggactcc cgcagacaca    3840
ggtcacggca ctgtggtgtt ggaattgcag tacactggca cggatggacc ttgcaaagtt    3900
cctatctcgt cagtggcttc attgaacgac ctaacgccag tggcagatt ggtcactgtc    3960 aaccctttg tttcagtggc cacggccaac gctaaggtcc tgattgaatt ggaaccaccc    4020
tttggagact catacatagt ggtgggcaga ggagaacaac agatcaatca ccattggcac    4080
aagtctggaa gcagcattgg caaagccttt acaaccaccc tcaaaggagc gcagagacta    4140
gccgctctag agacacagc ttgggacttt ggatcagttg gagggggtgtt caccctcagtt    4200 gggaaggctg tctaatgcgc gcggtacctt taagaccaat gacttacaag gcagctgtag    4260
atcttagcca cttttttaaaa gaaaagggg gactggaagg gctaattcac tcccaacgaa    4320
gacaagatcg tcgagagatg ctgcatataa gcagctgctt tttgcttgta ctgggtctct    4380
```

```
ctggttagac cagatctgag cctgggagct ctctggctaa ctagggaacc cactgcttaa    4440
gcctcaataa agcttgcctt gagtgcttca agtagtgtgt gcccgtctgt tgtgtgactc    4500
tggtaactag agatccctca gacccttta gtcagtgtgg aaaatctcta gcagt         4555
```